US012246136B2

(12) United States Patent
de Goeij et al.

(10) Patent No.: US 12,246,136 B2
(45) Date of Patent: Mar. 11, 2025

(54) HAPTIC RESPIRATION SIMULATOR WITH NOISE REDUCING PUMP SUSPENSION

(71) Applicant: Somnox Holding B.V., Rotterdam (NL)

(72) Inventors: Luc Johan Ries de Goeij, Delft (NL); Herman Pieter Modderman, Delft (NL); Marijn Leneman, Delft (NL); Clément Heinen, Delft (NL); Stijn Jeroen Antonisse, Delft (NL); Lucas Jan Bolier, Delft (NL)

(73) Assignee: Somnox Holding B.V., Rotterdam (NL)

( * ) Notice: Subject to any disclaimer, the term of this patent is extended or adjusted under 35 U.S.C. 154(b) by 885 days.

(21) Appl. No.: 17/424,320

(22) PCT Filed: Feb. 6, 2020

(86) PCT No.: PCT/NL2020/050065
§ 371 (c)(1),
(2) Date: Jul. 20, 2021

(87) PCT Pub. No.: WO2020/162750
PCT Pub. Date: Aug. 13, 2020

(65) Prior Publication Data
US 2022/0152340 A1    May 19, 2022

(30) Foreign Application Priority Data

Feb. 7, 2019   (NL) ...................... 2022527
Feb. 7, 2019   (NL) ...................... 2022528

(51) Int. Cl.
*A61M 21/02* (2006.01)
*A61M 21/00* (2006.01)
(52) U.S. Cl.
CPC ..... *A61M 21/02* (2013.01); *A61M 2021/0022* (2013.01); *A61M 2021/0088* (2013.01); *A61M 2205/07* (2013.01); *A61M 2205/42* (2013.01)

(58) Field of Classification Search
CPC .......... A61M 21/02; A61M 2021/0022; A61M 2021/0088; A61M 2205/07;
(Continued)

(56) References Cited

U.S. PATENT DOCUMENTS 4,606,328 A   8/1986   Thoman
5,167,610 A   12/1992  Kitado et al.
(Continued)

FOREIGN PATENT DOCUMENTS

CN   108078565 A   5/2018
CN   109222539 A   1/2019
(Continued)

OTHER PUBLICATIONS

Chinese Patent Application No. 202080017738.2, First Office Action, Mar. 28, 2023, 13 pages.
(Continued)

*Primary Examiner* — Sunita Reddy
(74) *Attorney, Agent, or Firm* — Hoffmann & Baron, LLP

(57) ABSTRACT

A haptic respiration simulator includes: a pump unit; an accumulator for reducing noise originating from a pumping action of the pump, the accumulator being in fluid communication with an outlet of the pump; and a pump suspension system for reducing noise originating from operation of the pump, including: a tubular casing for receiving the pump unit at an inside thereof, the tubular casing having a substantially closed circumferential wall that prevents at least a part of the sound waves resulting from operation of the pump to transfer outside the tubular casing; an inner suspension for suspending the pump with respect to the tubular casing, the inner suspension being positioned between the pump and the tubular casing; a pair of end caps for sealing the tubular casing, and an outer suspension for suspending the tubular casing with respect to a housing.

15 Claims, 13 Drawing Sheets

(58) Field of Classification Search
CPC ...... A61M 2205/42; A61M 2021/0016; A61M
2021/0044; A61M 2021/0066; A61M
2205/3306; A61M 2205/332; A61M
2205/3375; A61M 2205/3592; A61M
2205/502; A61M 2205/52; A61M
2205/586; A61M 2205/587; A61M
2205/8206; A61M 2230/06; A61M
2230/10; A61M 2230/205; A61M
2230/42; A61M 2230/432; A61M
2230/50; A61M 2230/63; G09B 19/00
USPC ..................................................... 600/26–28
See application file for complete search history.

(56) References Cited

U.S. PATENT DOCUMENTS

| | | | |
|---|---|---|---|
| 8,220,089 | B1 | 7/2012 | Diefenbach |
| 2006/0102171 | A1* | 5/2006 | Gavish ................. A61B 5/4818 128/95.1 |
| 2007/0179334 | A1 | 8/2007 | Groves et al. |
| 2007/0244370 | A1 | 10/2007 | Kuo et al. |
| 2008/0319334 | A1 | 12/2008 | Yamamori |
| 2011/0034756 | A1 | 2/2011 | Hacking et al. |
| 2011/0301405 | A1 | 12/2011 | Cho |
| 2013/0338428 | A1 | 12/2013 | Haisma et al. |
| 2014/0148872 | A1 | 5/2014 | Goldwasser et al. |
| 2016/0270948 | A1* | 9/2016 | Hariri .................. A61H 9/0078 |
| 2016/0331305 | A1* | 11/2016 | Krans .................... A61B 5/486 |
| 2022/0047841 | A1* | 2/2022 | Durán Vargas ...... A61H 9/0078 |

FOREIGN PATENT DOCUMENTS

| | | |
|---|---|---|
| JP | 2000-254358 A | 9/2000 |
| JP | 2013-13946 A | 1/2013 |
| KR | 10-2018-0095253 A | 8/2018 |
| WO | 2013/154009 A1 | 10/2013 |
| WO | 2014/061789 A1 | 4/2014 |
| WO | 2016/083391 A1 | 6/2016 |
| WO | 2017/194450 A1 | 11/2017 |
| WO | 2018/186739 A1 | 10/2018 |

OTHER PUBLICATIONS

Potenza, Alessandra, "For $500, this 'breathing' robot might help you sleep better", The Verge, Dec. 19, 2017, 5 pages.

* cited by examiner

HAPTIC RESPIRATION SIMULATOR WITH NOISE REDUCING PUMP SUSPENSION

CROSS-REFERENCE TO RELATED APPLICATIONS

This application is the National Stage of International Application No. PCT/NL2020/050065, filed Feb. 6, 2020, which claims the benefit of Netherlands Application Nos. 2022527, filed Feb. 7, 2019, and U.S. Pat. No. 2,022,527, filed Feb. 7, 2019, the contents of all of which are incorporated by reference herein.

FIELD OF TECHNOLOGY

The present invention relates in first aspect to a haptic respiration simulator, e.g. in the form of a pillow or a teddy, comprising a noise reducing pump suspension.

BACKGROUND

US2011/0301405 discloses a sleeping inducer in the form of a pillow or a doll, comprising a movable plate arranged inside a cover. The moving plate can repeatedly and vertically be moved by moving means. This way, the sleeping inducer can move like a lung that shrinks and expands. In another embodiment a pad filled with air is contained in the cover, between the moving plate and the cover. By moving the moving plate, the pad shrinks and expands. A user of the sleeping inducer, upon going to bed, hugs, grips or touches the sleeping inducer and has an experience resembling being hugged and slept by a mom.

It is a disadvantage of such sleeping inducers that they produce noise or sounds by operating the moving means. This noise may be experienced as annoying by users, especially when they use the sleeping inducer to try and fall asleep more easily in an otherwise quiet bedroom.

The general object of the first aspect of the present invention is to at least partially eliminate the above mentioned drawback and/or to provide a usable alternative. More specifically, it is an object of the invention to provide a haptic respiration simulator that is silent, e.g. that produces sounds not exceeding average bedroom-level sounds.

SUMMARY OF THE INVENTION

According to the first aspect of the invention, this object is achieved by a haptic respiration simulator as described herein.

When the haptic respiration simulator is used, i.e. when the pump unit is operated, sound or noise is inherently produced. The applicant has found that this noise mainly stems from four different sources. Firstly, providing small air pulses by operating the pump unit results in a vibration of air inside an air tube that connects the pump unit with the air chamber or other components. These vibrations result in sound waves which can be heard by a user. Secondly, the pump unit may physically move when it is operated. This movement of the pump unit results in a vibration of the air that surrounds the pump unit. This vibrating air results in sound waves which can be heard by a user. Thirdly, when the pump unit is operated, it may touch other (hard) components of the haptic respiration simulator. Also this touching or hitting of (hard) components produces sounds. Fourthly, the resonating vibration of certain components of the haptic respiration simulator, activated by vibrating air, may also result in sound, just like the vibration of a speaker diaphragm.

To optimally silence the haptic respiration simulator, each of these sources of noise should be prevented, reduced or dampened, such that a user of the simulator does not hear this noise while using the haptic respiration simulator. Ideally, a user cannot hear the simulator when he or she is in a silent environment, such as a bedroom, and uses the haptic respiration simulator. Preferably, the resulting noise produced by the simulator is reduced to below 40 dBA, more preferably to below 37dBA, e.g. to about 32dBA or less when measured at a position outside of the haptic respiration simulator, at a distance of 25 cm. This distance approximates the distance between ears of the user and the haptic respiration simulator in a normal or conventional operational mode of the haptic respiration simulator.

As a first noise-reducing measure, the haptic respiration simulator may comprise at least one accumulator for accumulating air and for reducing noise originating from a pumping action of the pump unit, i.e. for reducing the first source of sound described in the above. When seen in flow direction, the accumulator is arranged between the pump unit and the inflatable air chamber. In other words: the accumulator is in fluid communication with an outlet of the pump unit and an inlet of the inflatable air chamber.

The accumulator accumulates or buffers air in an internal volume thereof. The accumulator receives, in operation, pulses of air from the pump unit and supplies a stream of air to the inflatable air chamber. The accumulator thus smoothens the pulse-wise supply of air by the pump unit into a more constant stream of air supplied to the inflatable air chamber. This reduces the amount of noise generated by the haptic respiration simulator.

The haptic respiration simulator may further comprise a pump unit suspension system for reducing noise originating from operation of the pump unit, i.e. the second, third and fourth source of sound described in the above. The pump unit suspension system may damp sound waves resulting from physical movement of the pump unit when operated and damps or prevent sounds induced by (hard) components that touch or hit each other during operation of the pump unit. The suspension system may furthermore stabilize each component thereof to prevent it from vibrating like a speaker diaphragm.

The pump unit suspension system may comprise a tubular casing, an inner suspension, a pair of end caps, and an outer suspension. The inner suspension and the end caps are at least partly arranged inside the tubular casing, such that the tubular casing, the inner suspension and the end caps together encapsulate the pump unit and prevent sound waves from transferring outside of the tubular casing.

The tubular casing, which preferably has a substantially closed circumferential wall but which may have open ends to allow tubes and wires associated with the pump to protrude from the tubular casing, is more preferably thick-walled and made of a dense and heavy material such as steel (see below for more details). The inner suspension is preferably made of a less dense and less heavy material than the tubular casing (see below for more details). The use of such a double-layered sound isolation comprising a tubular casing and an inner suspension ensures that sound waves resulting from operating the pump unit must transfer trough two separate barriers before they can radially escape out of the tubular casing, out of the haptic respiration simulator, and produce sound that can be heard by a user. This double-layered sound isolation of the pump unit suspension system is more efficient than a relatively thicker layer of a single material, as the first barrier and the second barrier may advantageously each prevent the transmission of different frequencies of sound waves, while also having different critical frequencies themselves.

Preferably, the tubular casing furthermore is made of a heavy, dense material such as steel, such that the pump unit suspension system is stabilized by the mere weight of the tubular casing and vibrations of components are prevented. This further prevents or reduces sound emitted by the haptic respiration simulator.

The inner suspension, besides acting as a barrier for sound waves as described in the above, additionally suspends the pump unit with respect to the tubular casing and e.g. ensures that the pump unit remains at a central position in the tubular casing. The inner suspension thereby e.g. prevents the pump unit to physically touch the tubular casing when it is operated.

The end caps, arranged at each end of the tubular casing, may prevent an axial transfer of sound waves outside of the tubular casing by sealing the tubular casing. A first end cap and a second end cap of the pair of end caps may be similar, e.g. having a same diameter, and being made of the same material. The two end caps of the pair of end caps may however also be different from each other, e.g. when the one end of the tubular casing is differently shaped with respect to the other end of the tubular casing, or e.g. made of different materials. Each of the end caps seals one end of the tubular casing, and is arranged at that end.

The outer suspension is provided at the outside of the tubular casing, e.g. against the circumferential wall of the tubular casing and suspends the tubular casing with respect to the housing. The outer suspension is thus arranged between the tubular casing and the housing, and prevents the transfer of sound waves or vibrations from the tubular casing to the housing. Additionally, the outer suspension may provide a third barrier between sound waves originating from operation of the pump and transferred outside of the tubular casing towards ears of the user.

These combined features of an accumulator and a pump unit suspension system, as described, together help to prevent, reduce or damp the noise produced by the haptic respiration simulator when the pump unit is working, to a noise level hearable by a user that is preferably at or below bedroom-level sound, e.g. below 40 dBA, preferably below 37 dBA.

In embodiments, e.g. when the pump unit may be silently operated in view of pulses of air and/or when the pump unit is able to provide a constant (silent) air stream, the accumulator may be optional. The pump unit may be fluidly connected to the inflatable air chamber without an accumulator. The accumulator provided as a separate item to be fluidly connected in between the pump unit and the inflatable air chamber is optional. An accumulator may also be provided by an substantially airtight volume situated inside the assembly of the pump unit suspension system in between an outlet of the pump unit and an inlet conduit upstream the inflatable air chamber. The accumulator may be formed by a volume surrounding the pump unit in the assembly. In particular, the accumulator may be formed by a closed chamber of the inner suspension in which the chamber has a port for connecting the outlet of the pump unit and a port for pressurising the inflatable air chamber. An accumulator may be formed by an airtight compartment integral with an end cap in which the compartment is situated in between the outlet of the pump unit and an inner side of an end cap in which the compartment is provided with an outlet in fluid connection with the inflatable air chamber.

In embodiments, e.g. when the tubular casing comprises one or two end walls, e.g. of the same material as the circumferential wall thereof, one or both of the pair of end caps may be optional.

In embodiments, e.g. when the housing is at least partially made of a soft or resilient material, e.g. at the location of the tubular casing, the outer suspension may be optional.

In embodiments the inner suspension and the end caps may be integrated into a single component, as will be described in more detail below.

In embodiments, e.g. when a suspension suspends the pump unit with respect to the housing, the tubular casing may be optional.

In embodiments, e.g. when all components of the haptic respiration device which are arranged inside the housing are also arranged inside the tubular casing, the tubular casing may define the housing of the haptic respiration device.

The haptic respiration simulator, which is suited for relaxing a user by simulating a respiration that can be sensed by a body part, e.g. a hand, of the user, may e.g. be a sleep induction device, a stress relief device or a relaxation device. The haptic respiration simulator may e.g. be grabbed, hugged, touched, or contacted in another way by a user thereof. For example, the haptic respiration simulator may be formed as a pillow or a doll, e.g. having a peanut shape of a sleep induction device as disclosed in WO2018186739. In use, the user feels a movement of the haptic respiration simulator, which movement resembles a respiration of a person. More particularly, continuous inflation and deflation of the inflatable air chamber results in a movement of the haptic respiration simulator which is recognized by the user as a simulation of a respiratory action of a human. Preferably the simulated respiration has a relatively low frequency, around the frequency that an average person has when he or she is asleep. By using the haptic respiration simulator, and experiencing the low frequency respiration simulation, a user relaxes and may e.g. fall asleep or relieve stress during a busy day.

The haptic respiration simulator comprises a housing for housing components. The housing may at least partially be made of a rigid plastic material, e.g. formed by an injection moulding process. In embodiments, the housing and/or the haptic respiration simulator has a peanut-shape. In embodiments, the housing is covered with a layer of foam material, the haptic respiration simulator e.g. having a soft touch. The housing may have in internal volume in which components of the haptic respiration simulator, e.g. the pump unit, the accumulator or accumulators, the pump unit suspension system, and electronics may be placed.

The haptic respiration simulator comprises an inflatable air chamber, e.g. outside of the housing or integrated with an external wall of the housing, which is configured to simulate a respiration, e.g. of a user or a person, by repeated inflation and deflation. The inflation and deflation of the inflatable air chamber may be noticed by a user of the haptic respiration simulator when holding the simulator in hands of the user; the deflation and inflation of the air chamber resembling a respiration of a person.

The haptic respiration simulator comprises a pump unit that is positioned inside the housing. The pump unit supplies air to the accumulator and is, indirectly, in fluid communication with the inflatable air chamber, such that it can pump a volume or air into the inflatable air chamber.

In an embodiment, the tubular casing is hollow and has open ends, is made of steel and is thick-walled, i.e. has a thickness of at least 1 mm, e.g. 1.5 mm or 2 mm. The tubular casing may be hollow to allow it to receive other components of the haptic respiration simulator therein, for example the inner suspension, the pump unit and/or the accumulator. The tubular casing may be made of thick-walled steel to prevent sound waves to escape from the tubular casing in a radial direction. When the tubular casing is heavier (i.e. made of a more dense material and/or thicker), it is more difficult for sound waves to transfer through the tubular casing. Additionally, the weight of thick-walled steel also stabilizes the tubular casing, to reduce and/or prevent resonating vibrations of any components of the haptic respiration simulator.

Alternatively, the tubular casing may also be made of other materials or have another thickness. For example, the tubular casing may be made of a material having a density that is about ⅓ of the density of steel, while being three times as thick, e.g. at least 3 mm. An example of such a material is aluminium. Of course, other materials may be chosen according to the same principle. E.g. a material that is 10% denser than steel, and 10% thinner.

In an embodiment, the inner suspension comprises at least three resilient elements, arranged at different positions along the circumference of the pump unit, the at least three resilient elements suspending the pump unit about a central position in an internal volume of the tubular casing. The inner suspension may comprise at least three spring-like resilient elements, e.g. for suspending the pump unit at three or more discrete positions along the circumference of the pump unit.

In an embodiment, the inner suspension comprises a resilient material, e.g. silicon, that surrounds the pump unit, at least in a circumferential direction thereof. The inner suspension may e.g. be wrapped around the pump unit, to physically separate it from the tubular casing. By wrapping the pump unit in a resilient material, the resilient material acts as a suspension for the pump unit with respect to the tubular casing. The resilient material may lie against the pump unit with one side thereof, while it may lie against an inner side of the tubular casing with another, opposing, side thereof.

In an embodiment, the inner suspension and the end caps are made of the same material and are integrated with each other. For example, an inner circumferential wall of the end caps may be embodied as inner suspension. With this arrangement, the number of parts is reduced, which may result in a lower overall cost. Additionally, assembly of the pump unit suspension system may be quicker with less parts, which again may result in a lower overall cost.

Furthermore, when the inner suspension and the end caps are integrated, the inner suspension may be relatively thin. As a result, the inner diameter of the tubular casing may be smaller, which saves weight. This makes the haptic respiration simulator lighter, which may be more comforting for users thereof.

The inner suspension and the end caps may also be integrated while being made of different materials. For example, an end cap with integrated inner suspension may be made using a 2K injection moulding process, wherein two different materials may be used to produce the end cap.

In an embodiment, the pump unit suspension system comprises a second tubular casing, a second inner suspension and a second pair of end caps for suspending a subassembly of a first tubular casing, a first inner suspension, and a first pair of end caps. Such a double arrangement is beneficial in that an additional acoustic decoupling is provided which further reduces a transfer of vibrations.

In an embodiment, the end caps have a double-walled circumferential wall that protrudes towards the pump unit when the pump unit suspension system is assembled, an inner wall of the double-walled circumferential wall e.g. being arranged against an inner side of the tubular casing, an outer wall of the double-walled circumferential wall e.g. being arranged against an outer side of the tubular casing. The inner wall may then form the inner suspension and/or the outer wall may then form the outer suspension. This specific embodiment may result in less parts and faster assembly, saving costs.

In an embodiment, the outer suspension comprises foam material, e.g. at least six blocks of foam material, provided at different locations along the circumferential wall of the tubular casing, between said wall and the housing. It is not required that the outer suspension fully surrounds the tubular casing, although this is possible. The outer suspension may comprise a number of different suspensive elements, that are positioned at several discrete locations along the circumferential wall of the tubular casing.

In an embodiment, the haptic respiration simulator further comprises a second accumulator for accumulating air and for (further) reducing noise originating from a pumping action of the pump unit, the second accumulator being in direct fluid communication with an outlet of the first accumulator and an inlet of the inflatable air chamber, and in indirect fluid communication with the pump unit. In streamwise direction, starting at the outlet of the pump unit, air may go from the pump unit to the first accumulator, then to the second accumulator, before entering the air chamber. The haptic respiration simulator may comprise more than two accumulators.

The first and second accumulator may be integrated in a single component, e.g. separated by a partition.

In an embodiment, at least one of the accumulators or the accumulator may be positioned inside the housing, outside of an internal volume of the tubular casing. That is, the only accumulator may be positioned outside an internal volume of the tubular casing, both or all accumulators may be positioned outside an internal volume of the tubular casing, or a subset of all accumulators may be positioned outside an internal volume of the tubular casing, while other accumulators, if present, may be positioned inside the tubular casing. When one or more of the accumulators are positioned outside the tubular casing, the internal volume of the tubular casing required to house all components may be smaller. As a result, the diameter of the tubular casing may be smaller or its length may be shorter, resulting in a lighter part. As the weight of the tubular casing may make up a significant portion of the weight of the haptic respiration simulator, e.g. 5%-25%, reducing the weight of the tubular casing may significantly reduce the weight of the haptic respiration simulator.

In an embodiment, the inflatable air chamber is positioned external of the housing, to optimally transfer the respiration simulation to a body part of a user. The inflatable air chamber may also be arranged as part of the housing. Alternatively, the air chamber may be arranged inside the housing, e.g. against a part of the housing that is made of a flexible material, such that the inflation and deflation of the air chamber can be sensed by a user. Preferably, the inflatable air chamber is positioned at the outer side of the housing.

In the first aspect, the invention further relates to a method for relaxation of a user, wherein use is made of the haptic respiration simulator as described above.

In the first aspect, the invention further relates to a method for guiding a user towards a sleep state, wherein use is made of the haptic respiration simulator as described in the above.

Field of Technology Second Aspect

According to a second aspect, the invention relates to a relaxation monitoring device for monitoring a physiological characteristic of a user during relaxation.

Background Art for Second Aspect

U.S. Pat. No. 5,167,610 discloses a sleep inducing system which employs a respiration as a biological signal for shifting a person organically into a state of sleep in accordance with a respiration cycle. The sleep inducing system is capable of realising a sleep induction smoothly within a short time. The sleep inducing system comprises a respiration detecting section and a control unit to which a stimulus output means is connected through a driving circuit means. The respiration detecting section includes a respiration sensor. The respiration sensor is provided in a shape mountable to the person's abdominal or chest region without substantial feeling of foreign matter or unpleasantness for detecting variation in the region's bulginess by means of a strain gauge or the like. For the detection, a bed sheet type strain gauge, a thermistor type sensor disposed in a zone where nose exhalation is sensible enough for detecting thermal change or like means may also be employed.

The stimulus output means employs, for example, a light emitting means. A brightness of the light emitted by the stimulus output means may be caused to vary to be bright and dark during the awakening period in conformity to the respiration rhythm, so that the brightness will be gradually elevated upon the inhalation but will be gradually lowered upon the exhalation. An open loop control is carried out for gradually darkening with time up to a time when a detection of the respiration rhythm can be discriminated to be an indication of the state in which the person has fallen asleep. Then a feedback control is carried out for providing the light stimulus as adapted to the deepness of the sleep immediately after the discrimination of the fallen-asleep state. Further, it is disclosed that alternatively to a stimulus being light, the stimulus may be any of sound, vibration, wind, fragrance and the like.

A drawback of the known sleep inducing system is that the system lacks accuracy. The bed sheet type strain gauge or thermistor type sensor is to be disposed in a zone of nose exhalation. However, in practice, a person is moving around in his bed and switches sides which negatively affects the detection of the respiration cycle. Attaching the sensor to the person's abdominal or chest may provide a more accurate detection, but in practice, such an attached sensor remains a disturbing item, is more vulnerable to get damaged and attaching a sensor to a person's body is experienced as inconvenient and bothersome when a person wants to go to bed.

WO2017/194450 discloses a sleep monitoring system for monitoring a sleep of a subject. The sleep monitoring system comprises a $CO_2$ sensor and a processor communicatively coupled to the $CO_2$ sensor. The processor is adapted to monitor a $CO_2$ concentration from sensor data produced by the $CO_2$ sensor to derive sleep pattern information, such as an indication that the subject is awake or asleep. The sleep pattern information can be derived without having to contact the subject being monitored. A sensor device is provided which comprises the $CO_2$ sensor. The sensor device may be a stand-alone device, e.g. a sensor box, that may be positioned in close vicinity to the subject to be monitored. The sensor device may be dimensioned such that it can be clipped or otherwise secured to a bed, e.g. to a headboard of the bed, in which the subject sleeps. As illustrated in FIG. 8, a sleep monitoring system is embodied by an air purification apparatus having a fan positioned at an air inlet to drive an air flow along an air purification path to an air outlet. The sensor device including the $CO_2$ sensor is integral to the air purification apparatus.

The known sleep monitoring system may further comprise a sensory output device to generate a sensory stimulus in response to an identified sleep phase. A sensory stimulus like a pleasant and calming sound or perfume scent may be released in a confined space in order to enhance or improve that particular sleep phase of the sleeping subject.

A drawback to this known sleep monitoring system is that also in this sleep monitoring system the monitoring of the $CO_2$ concentration lacks accuracy. The monitoring is negatively affected when a person is moving around or switching sides before falling asleep, i.e. when a head of a person is closer or farther away from the sensor device at the headboard of the bed.

WO2018186739 discloses a sleep induction device for inducing changes during a sleep session of a user, wherein the sleep induction device comprises at least one sensor for detecting a physiological characteristic of the user, a stimulator which is configured to provide successive stimuli to the user to anticipate on the detected physiological characteristic. The sleep induction device has an outer shape which is formed as a peanut-shaped pillow.

A drawback of this known sleep induction device is that poor measurements of a physiological characteristic may be obtained when the device is not used as intended.

Regarding this second aspect of the invention, the general object is to at least partially eliminate the above mentioned drawbacks and/or to provide a usable alternative. More specifically, it is an object of the invention to provide a relaxation monitoring device having an improved accuracy in measuring a psychological characteristic which accuracy is less dependent of a position and orientation of the relaxing user.

Summary of Second Aspect

According to the second aspect of the invention, this object is achieved by a relaxation monitoring device according to clause 1.

According to the second aspect of the invention, a relaxation monitoring device is provided for monitoring a physiological characteristic of a user. The relaxation monitoring device is portable and is configured to be used during relaxation in which a user desires to take some rest. In particular the monitoring device is configured to be used during a sleep session. The relaxation monitoring device can be used while sitting on a bench or lying on a mattress. When lying, the monitoring device is to be used in front of the user's body and preferably in front of the chest such that the device is close to the user's face. When sitting on a bench, the relaxation monitoring device is to be held in front of the user on its lap to obtain accurate measurements.

The relaxation monitoring device comprises a cushion. The cushion has an outer surface which provides a cushioning to support a human hand of the user. Seen in a top view, the cushion defines an outer shape of the device. Seen in a top view means a projection from above onto the device in which the product is in a stable put away position, e.g. laid down on a mattress or put aside on a table besides a sofa. In the top view projection, the device is in a stable position as it may lie on a mattress as shown in FIG. 1. The outer shape is elongated along a longitudinal axis. A head portion and a tail portion of the outer shape are defined in which the head portion has a length along the longitudinal axis which equals a length along the longitudinal axis of the tail portion. In other words, the head portion and the tail portion subdivide the outer shape into substantially equal portions. In use during a relaxation session, the user holds the device close to the user's body. The head portion is to be directed to a face of the user and the tail portion is directed away from the face to an abdominal or legs of the user.

The relaxation monitoring device comprises a housing for housing components of the device. The housing is positioned inside the cushion. Preferably, the cushion completely surrounds and covers the housing, such that the device is soft all around to be used as a pillow. The cushion may comprise a cushion layer which may be a foamed layer. The housing comprises an outer shell. The outer shell provides rigidity to at least a part of the outer shape of the device. The outer shell delimits an inner space for containing electrical components, like a battery, a motor, an air-pump, a control unit etc.

The relaxation monitoring device comprises at least one sensor for monitoring the physiological characteristic of the user. The at least one sensor is positioned in the head portion of the outer shape of the device, such that in use the at least one sensor can be positioned close to the face of the user.

The relaxation monitoring device comprises a control unit connected to the at least one sensor for receiving a sensor signal from the at least one sensor. Preferably, the control unit is connected to a memory for storing sensor data measured by the at least one sensor.

According to the second aspect of the invention, the at least one sensor comprises a respiratory sensor. The respiratory sensor is configured to monitor an exhaled air flow from the user. The respiratory sensor is configured for measuring properties of a gaseous medium contacting the sensor. Preferably, the respiratory sensor is a CO2 sensor for monitoring a CO2 concentration in the exhaled airflow. The respiratory sensor is in fluid communication with an outside of the device by at least one air passageway. The at least one air passageway is configured to allow the exhaled airflow from the user flowing from the outside of the device to the respiratory sensor. The at least one air passageway is provided at the head portion. The at least one air passageway is emerging at the head portion. The at least one air passageway is provided at a side of the outer shape of the device which side is in use to be directed towards the user. Hereafter, the side of the relaxation monitoring device which in use is to be directed towards the user is called a user side. The at least one air passageway is emerging at the user side. The at least one air passageway has an air opening positioned on the user side. The positioning of the at least one air passageway at the head portion and more specific at the user side contributes to a higher level of an accuracy in measurements of the exhaled airflow.

The relaxation monitoring device according to the second aspect of the invention is improved by an implementation of a first and second feature which contribute to a correct orientation of the device during use. In the correct orientation of the device during use the at least one air passageway is correctly directed to the face of the user. The at least one air passageway may be covered by a pillow-case or a room may be darkened such that a user might have a difficulty to visibly orient the device in a right manner. A first feature stimulates that the head portion instead of the tail portion of the device is directed to the face of the user. A second feature stimulates that the user side of the head portion which is provided with the sensor/air passageway will intuitively be directed towards the user.

The first feature contributing to a correct orientation of the device during use is that a centre of gravity of the relaxation monitoring device is positioned in the tail portion of the outer shape. In preparing for a relaxation session, when the user takes the device to bed or a relaxing chair, due to a natural tendency to keep a centre of gravity low when carrying a product, the relaxation monitoring device will be held by the user in a predetermined orientation, in which the head portion is held upwards and the tail portion is held downwards. Herewith, the head portion will automatically be directed to the face of the user as it is desired for a proper use of the relaxation monitoring device. When holding the device close to the user's body, the tail portion will then be directed to an abdominal of the user's body.

The second feature contributing to a correct orientation of the device during use is defined by a hand pad for supporting the human hand. The relaxation monitoring device comprises a hand pad which is positioned at a side of the outer shape of the relaxation monitoring device which side is in use facing away from the user. This user facing away side is also called a 'hand pad side'. The hand pad side of the relaxation monitoring device is positioned opposite the 'user facing side' or simply 'user side' which user side is provided with the at least one air passageway.

The elongated outer shape has an outer contour which includes a concave portion. The concave portion forms a hand pad to support the human hand during the sleep session. Preferably, the concave portion has a width which substantially equals a width of a human hand. The concave portion may be formed by an ergonomic portion corresponding with a human hand shape for accurately positioning the human hand onto the device.

A main advantage of the relaxation monitoring device according to the second aspect of the invention is that a use of the device in a correct orientation is improved. The user will intuitively use the device in a correct orientation. The positioning of the centre of gravity in the tail portion and the presence of the hand pad contribute to a proper orientation of the device. The proper orientation of the device ensures that the at least one air passageway for receiving the exhaled air flow is directed towards the face of the user which may increase an accuracy and reliability of the monitoring of the physiological characteristic of the user.

An advantage is that the presence of the hand pad at the side of the relaxation monitoring device facing away from the user is that this hand pad stimulates the user in a natural manner to attract the relaxation monitoring device towards the user's body. The user is encouraged to embrace the device with his hand. In a sitting posture on a relaxing chair, the hand pad stimulates the user to keep the device with the head portion upwards and to attract the device to the user's body. In a lying posture, the hand pad stimulates a posture of the user in which the user is laying in a spooning arrangement with the relaxation monitoring device. The user is stimulated to sleep in a physical contact with the relaxation monitoring device. Preferably, the user side of the relaxation monitoring device is convex shaped which further stimulates the spooning arrangement. Herewith, the relaxation monitoring device is positioned close to the user which further contributes to an accurate measurement of the physiological characteristic.

In an embodiment of the relaxation monitoring device according to the second aspect of the invention, the respiratory sensor is a CO2 sensor for measuring a CO2 concentration in the exhaled air flow flowing from the user. Advantageously, by measuring a CO2 concentration as a physiological characteristic, an accurate input may be obtained regarding a relaxing quality or sleep stage of a user.

In a further embodiment, the CO2 sensor may be a chip-shaped sensor. The chip-shaped sensor is mountable to a printed circuit board. The chip-shaped sensor is beneficial, because of its miniature size. Such a chip-shaped sensor to be positioned in the head portion of the device will hardly affect a position of a centre of gravity of the device. The printed circuit board may further contain the control unit and is configured to electronically connect the chip-shaped sensor to the control unit. Advantageously, the printed circuit board including the CO2 sensor provides a robust structure which can be firmly mounted to the housing of the relaxation monitoring device. An example of such a chip-shaped CO2 sensor is disclosed in WO2016/083391.

In an embodiment of the relaxation monitoring device, the centre of gravity of the device is positioned in a region in a lower half of a length of the tail portion along the longitudinal axis which lower half is positioned adjacent to a tail portion end face. Advantageously, the centre of gravity is positioned at a distance, in particular at least 5 cm, from a geometrical centre point of the outer shape. The centre of gravity is spaced from the hand pad, such that a moment of inertia is generated when picking up the device to bring the device in an upright position. Preferably, the centre of gravity is positioned in between the longitudinal axis and the user side to stimulate an intuitive rotation of the device when picking up. More in particular, the centre of gravity is positioned in a region in between the longitudinal axis and the outer contour, which region is spaced at a perpendicular distance from the longitudinal of at least 20% away from the longitudinal axis.

In an embodiment of the relaxation monitoring device, the respiratory sensor is positioned in a region in an upper half of the length of the head portion along the longitudinal axis which upper half is positioned adjacent to a head portion end face.

In an embodiment of the relaxation monitoring device according to the second aspect of the invention, the relaxation monitoring device comprises a housing, a battery, a motor and a suspension for suspending the motor. Preferably, the motor is connected to a pump to form a pump unit which pump unit is connectable to an inflatable air chamber. The relaxation monitoring device may further comprise at least one accumulator for dampening vibrations originating from the pump unit. Preferably, at least the suspension assembled with the motor/pump unit is positioned inside the device, such that a centre of gravity of the assembled suspension is positioned in the tail portion. The assembled suspension is a considerable factor in a total weight of the device, such that the positioning of the assembled suspension in the tail portion contributes to obtain the centre of gravity of the device in the tail portion.

In an embodiment of the relaxation monitoring device according to the second aspect of the invention, the relaxation monitoring device comprises a light emitting element, in particular a control panel for controlling the device, which is positioned at the hand pad side of the relaxation monitoring device. Preferably, the control panel is positioned adjacent the hand pad at the tail portion of the relaxation monitoring device to increase the centre of gravity in the tail portion. The control panel may include a light-emitting element, like a display or LED which is advantageously directed away from the user during sleep. Besides the control panel, the relaxation monitoring device may comprise any other light-emitting element which is preferably positioned at the hand pad side.

In an embodiment of the relaxation monitoring device according to the second aspect of the invention, the at least one air passageway extends from the outer surface through the cushion and the housing to the respiratory sensor. Preferably, the cushion comprises a cushion layer which covers the outer shell of the housing. The at least one air passageway may be formed by a through hole through the cushion layer and the outer shell. The at least one air passageway may have an air opening at the outer surface of the relaxation monitoring device. The air opening may have a diameter of at least 5 mm. The air opening may be fully open and non-covered. In particular, the cushion may comprise a pillow-case of a textile material to cover the air opening in the cushion layer. The pillow-case may comprise a seam, which is preferably closable by a razor, which seam is positioned in the assembly of the pillow-case across the at least one air passageway. Advantageously, due to the positioning of the razor across the at least one air passageway, the seam may be sufficient permeable for the airflow for flowing to the respiratory sensor while at the same time covering the at least one air passageway to prevent any non-desired intrusion. Preferably, the relaxation monitoring device comprises a group of at least two air passageways to increase a reach for receiving the exhaled air flow. Preferably, the at least two air passageways are linearly aligned in an array along the user side.

In an embodiment of the relaxation monitoring device according to the second aspect of the invention, the relaxation monitoring device is arranged as a hand-pillow. The hand-pillow is configured as small as possible and just adapted to comfortably support the human hand. The hand-pillow may have a total volume of that most 10 liters, preferably at most 5 liters. Herewith, the hand-pillow is advantageously sized to be taken into bed or when sitting in a relaxed chair to be held close to a user's body while relaxing.

In an embodiment of the relaxation monitoring device according to the second aspect of the invention, the user side is convex shaped. The outer shape may be an arc-shape. The head portion and the tail portion may be equally shaped. The head and tail portion of the outer shape may be circular. The head and tail portion may have a same radii. Also the concave hand pad side and convex user side may have a same radii. Preferably, the outer shape of the relaxation monitoring device has a kidney-shape, also called a jellybean shape, including a concave portion at the hand pad side and a convex portion at the user side. The concave portion may have a smaller radius than the convex portion and the tail end face may have a smaller radius than the head end face, such that the elongated outer shape forms an arc-shape. The centre of gravity may be positioned on an central arc-line defining the arc shape, in particular in a region within 3 cm of the arc-line. Advantageously, the kidney-shape of the relaxation monitoring device stimulates the spooning of the user and the device while sleeping, such that a sensor at the user side will be positioned close to the user's body, in particular close to the user's face, which contributes to the accuracy of measurements.

In an embodiment of the relaxation monitoring device according to the second aspect of the invention, the relaxation monitoring device comprises a stimulator. The stimulator is configured to improve a quality of a relaxing moment. The relaxation monitoring device is then not only arranged for monitoring a physiological characteristic of the user during the relaxing period, but is further arranged to enhance the relaxing moment. The stimulator may be arranged to create a comfortable atmosphere. The stimulator may for example be formed by a speaker to provide music.

In an embodiment of the relaxation monitoring device, the stimulator is configured for helping a person to fall asleep. The stimulator may be configured to improve a quality of a sleep session by providing successive stimuli to guide a user during a sleep session to manage and optimise a sleep pattern of a user. Herewith, the relaxation monitoring device is a sleep induction device. A sleep induction device may be arranged to induce a change during a sleep session of a user, in particular to let the user fall asleep. A change during a sleep session means a change from a first sleep state to a second sleep state. The change may for example be a change in a respiration rate during a NREM-sleep stage. It is noted that a sleep session, in the context of this document, spans the time period from getting ready to sleep, e.g. getting into bed or lying on a couch, until waking up, e.g. getting out of bed or stepping from the couch. In particular, the sleep induction device is arranged to induce a change, a so called sleep stage transfer, which means a change from a first sleep stage to a second sleep stage, e.g. from a light to a deep sleep stage or from a REM to a NREM sleep stage.

The stimulator of the sleep induction device may be configured to provide successive stimuli to the user during the sleep session. The stimulator may provide stimuli to the user continuously. The stimulator provides successive stimuli to anticipate on the detected physiological characteristics, to guide the user. Multiple stimulators may be comprised in the sleep induction device. Multiple stimulators may be active at the same time, the stimulators working in parallel.

In particular, the user is guided by the successive stimuli via a guidance path, the user following the guidance path to induce a change during the sleep session of the user, e.g. to guide a user from a first sleep state of the user to a second sleep state of the user. Preferably, the guidance path is configured to provide a smooth and timely transfer from the first sleep state to the second sleep state. It is noted that this 'following' the guidance path by the user is preferably done subconsciously.

The sleep induction device may comprise at least one memory for storing data during the sleep session. The memory is arranged to store values of detected physiological characteristics and provided stimuli during the sleep session. The memory may for example compute a historic record of the provided stimuli and the corresponding physiological characteristics. Preferably, this historic record is updated in real-time.

In an embodiment the sleep induction device comprises a processing unit, also called a control unit, for operating the device. The processing unit includes a control programme which is programmed to determine a current sleep state of the user during the sleep session. The current sleep state is based on at least one detected physiological characteristic measured by the at least one sensor. The current sleep state may depend on real-time measurements, and may also depend on the historic record of measurements, stored in the memory. For example, when transitioning from a light to a deep sleep, the heart rate of a user may slow down, to rise again when reaching REM sleep. Based on only the real-time measurements, it may be difficult to determine whether the user is awake or in REM sleep. For that reason, the current sleep state may be determined by the real-time measurements in combination with a historic record of measurements.

In an embodiment of the relaxation monitoring device according to the second aspect of the invention, the stimulator of the relaxation monitoring device is configured to provide a haptic stimulus via the hand pad. Advantageously, by providing haptic stimuli instead of audible stimuli, sounds which may be disturbing in falling asleep may be prevented. Preferably, the stimulator comprises an inflatable air chamber under the hand pad to provide the haptic stimuli. The air chamber is inflatable and deflatable to provide a respiration rhythm as a stimuli to the user. The air chamber is preferably positioned close to the outer surface of the device. Preferably, the air chamber is positioned under the hand pad, such that the haptic stimulus are directly transferred to a user's hand. Preferably, the air chamber is connected to a pump unit for frequently inflating the air chamber. Alternatively, the stimulator may comprise a stimulator mechanism for frequently expanding and collapsing a body, to provide a stimulating rhythm to the user to influence the user's respiration rate.

In an embodiment the relaxation monitoring device comprises a transfer element. The relaxation monitoring device may e.g. have a Bluetooth component or have a wifi-component to connect the device to a wireless network. By transferring a signal based on measurement data of at least one physiological characteristic, the relaxation monitoring device may be used to operate other devices. The relaxation monitoring device may for example be used to operate a relax chair, a wake-up device or to operate climate control devices to condition a room. Advantageously, a quality of the relaxation can be improved based on at least one measured physiological characteristic, such a physiological characteristic may be a respiration rate, heart rate, body activity, body temperature, brain activity or any other physiological characteristic which might be of interest to control a relaxation of the user.

Further, the second aspect of the invention relates to a monitoring method for monitoring a person during relaxation by using a relaxation monitoring device, wherein the method comprises the steps of:

providing a relaxation monitoring device according to any aspect of the invention;

picking up the relaxation monitoring device by placing a hand onto a hand pad of the relaxation monitoring device;

bringing the relaxation monitoring device in an operational orientation by attracting the relaxation monitoring device towards a person's body;

Further, the second aspect of the invention relates to a use of the relaxation monitoring device as a sleep inducing device for guiding a user in falling asleep and/or to guide the user during a sleep session to manage a sleep pattern.

Further, the second aspect of the invention relates to a use of the relaxation monitoring device for operating connected devices e.g. for operating a massage chair, massage tool, alarming device or climate device for climate control of a room.

According to a third aspect, the invention relates to a relaxation monitoring device for monitoring a physiological characteristic of the user during relaxation. The relaxation monitoring device comprises a cushion having an outer surface which provides a cushioning to support a body part, wherein the cushion defines an outer shape of the device which outer shape is elongated along a longitudinal axis, in which a head portion and a tail portion of the outer shape are defined in which the head portion has a length along the longitudinal axis which equals a length along the longitudinal axis of the tail portion the relaxation monitoring device comprises a housing for housing components of the device, which housing is at least partially covered by the cushion, wherein the housing delimits an inner space for containing electrical components, like a battery, a motor, an air-pump and a control unit. The relaxation monitoring device comprises at least one sensor for monitoring the psychological characteristic of the user, which at least one sensor is positioned at the head portion or tail portion of the outer shape of the relaxation monitoring device. The relaxation monitoring device comprises a control unit connected to the at least one sensor for receiving a sensor signal from the at least one sensor.

In particular, a centre of gravity of the relaxation monitoring device is positioned in the tail portion of the outer shape, such that in starting use—when picking up the device—due to a natural tendency the relaxation monitoring device will be held by the user in a predetermined orientation, in which the head portion is directed to a face of the user and the tail portion is directed to an abdominal of the user, such that the at least one sensor or another component, e.g. a display or speaker, is optimally positioned for operation of the relaxation monitoring device.

In particular, the cushioning is a hand pad for supporting a hand of a user. The hand pad is provided at hand pad side of the relaxation monitoring device. Beneficially, the hand pad contributes to a proper orientation of the device in use, such that a sensor or other component of the device will optimally operate. The proper orientation may contribute in achieving a high sensor accuracy.

In the third aspect of the relaxation monitoring device, the hand pad is provided at a hand pad side of the relaxation monitoring device, such that a sensor at the user side will be positioned close to the user's body, in particular close to the user's face, which contributes to the accuracy of measurements.

In an embodiment, the hand pad may be formed by a concave portion of the elongated outer shape. The elongated outer shape has an outer contour which includes a concave portion which forms a hand pad. The concave portion is positioned at a side of the outer shape which side is in use to be directed away from the user, such that in use due to a natural tendency the device will be held in a proper orientation. When the user places a hand onto the hand pad, the user has a natural tendency to attract the relaxation monitoring device towards the user's body.

In an embodiment, the hand pad may include a heating pad for warming a hand of the user. The heating pad may stimulate a user to place a hand in a correct manner on the device.

In an embodiment, the device may include a heating pad for warming the user's body which heating pad is positioned at a user side of the device. In particular, the heating pad is an electric heating pad including an electric heat circuit which electric heating pad is incorporated in the device. In particular, the heating pad may be connectable as a separate item to the device. The heating pad as a separate item may e.g. be connectable by hook-and-loop fasteners. The heating pad may for example include a heating pad constituent, like a heating powder or gel which can be activated by the user or preferably includes a more sustainable heating constituent like a heat pit which can be heated by microwaving the heat pad before use.

In an embodiment, the stimulator is positioned at the hand pad. Preferably, the stimulator is an inflatable air chamber positioned at an outer surface of the device and defining a position of the hand pad. The stimulator contributes in the tendency of a user to place a hand on the hand pad, such that the device gets oriented as intended.

In an embodiment, the relaxation monitoring device comprises a control panel and/or a display which is positioned at a side other than the user side, in particular at the hand pad side. The control panel and/or display positioned away from the user side may remain out of side when the user is laying aside the device which is beneficial in not disturbing the user.

In an aspect, the invention relates to a relaxation monitoring device for monitoring a physiological characteristic of a user during relaxation, comprising a cushion having an outer surface which provides a cushioning to support a human body part, in particular a human hand, wherein when seen in a top view the cushion defines an outer shape of the device which outer shape is elongated along a longitudinal axis, in which a head portion and a tail portion of the outer shape are defined in which the head portion has a length along the longitudinal axis which equals a length along the longitudinal axis of the tail portion; a housing for housing components of the device, which housing is at least partially covered by the cushion, wherein the housing comprises an outer shell which delimits an inner space for containing electrical components, like a battery, a motor, an air-pump and a control unit; at least one sensor for monitoring the psychological characteristic of the user, which at least one sensor is in particular positioned at the head portion of the outer shape of the relaxation monitoring device; a control unit connected to the at least one sensor for receiving a sensor signal from the at least one sensor.

In particular, the at least one sensor comprises a respiratory sensor for monitoring an exhaled air flow from the user, wherein at least one air passageway is provided at the head portion at a user side which is a side of the outer shape which side is in use to be directed towards the user which at least one air passageway is in fluid communication with the respiratory sensor to allow the airflow flowing from an outside of the device to the respiratory sensor;

In particular, a centre of gravity of the relaxation monitoring device is positioned in the tail portion of the outer shape, such that in starting use—when picking up the device—due to a natural tendency the relaxation monitoring device will be held by the user in a predetermined orientation, in which the head portion is directed to a face of the user and the tail portion is directed to an abdominal of the user.

In particular, the elongated outer shape has an outer contour which includes a hand pad which hand pad is positioned at a side of the outer shape which side is in use to be directed away from the user, such that in use due to a natural tendency the at least one passageway will be directed towards a face of the user when the user places a hand onto the hand pad and attracts the relaxation monitoring device towards the user's body. A concave portion to form a hand pad is preferred, but the hand pad may be provided by another feature, for example be indicated by a coloured portion of the hand pad side of the device. Providing a hand pad without the centre of gravity being positioned at the tail portion may still be beneficial to intuitively stimulate a correct orientation.

As described above, according to the second aspect of the invention, the at least one air passageway may be provided at the head portion at the user side of the relaxation monitoring device.

In a fourth aspect, the invention relates to a relaxation monitoring device for monitoring a physiological characteristic of a user during relaxation, comprising a cushion having an outer surface which provides a cushioning to support a human body part, in particular a human hand, wherein when seen in a top view the cushion defines an outer shape of the device which outer shape is elongated along a longitudinal axis, in which a head portion and a tail portion of the outer shape are defined in which the head portion has a length along the longitudinal axis which equals a length along the longitudinal axis of the tail portion; a housing for housing components of the device, which housing is at least partially covered by the cushion, wherein the housing comprises an outer shell which delimits an inner space for containing electrical components, like a battery, a motor, an air-pump and a control unit; at least one sensor for monitoring the psychological characteristic of the user, which at least one sensor is in particular positioned at the head portion of the outer shape of the relaxation monitoring device; a control unit connected to the at least one sensor for receiving a sensor signal from the at least one sensor.

According to a fourth aspect, the at least one sensor is a sensor for measuring a physiological characteristic. Instead of the respiratory sensor for monitoring a gaseous medium, the at least one sensor may comprise another type of sensor, e.g. an accelerometer or a temperature sensor provided at a functional location in the outer shape to achieve optimal measurement close to the user's body. The functional location requires the relaxation monitoring device to be used in a predetermined orientation. The at least one sensor may for example be positioned close to the user side, e.g. at a distance of at most 2 cm.

In particular, the at least one sensor comprises a respiratory sensor for monitoring an exhaled air flow from the user, wherein at least one air passageway is provided at the head portion at a user side which is a side of the outer shape which side is in use to be directed towards the user which at least one air passageway is in fluid communication with the respiratory sensor to allow the airflow flowing from an outside of the device to the respiratory sensor.

In particular, a centre of gravity of the relaxation monitoring device is positioned in the tail portion of the outer shape, such that in starting use—when picking up the device—due to a natural tendency the relaxation monitoring device will be held by the user in a predetermined orientation, in which the head portion is directed to a face of the user and the tail portion is directed to an abdominal of the user; and In particular, the elongated outer shape has an outer contour which includes a concave portion which forms a hand pad which concave portion is positioned at a side of the outer shape which side is in use to be directed away from the user, such that in use due to a natural tendency the at least one passageway will be directed towards a face of the user when the user places a hand onto the hand pad and attracts the relaxation monitoring device towards the user's body.

The at least one sensor for measuring a physiological characteristic may be any type of sensor which in dependence of its function requires a particular position in the device and in use a proper orientation of the device. In particular, the at least one sensor is a sensor selected from a group of sensors comprising a microphone, a temperature sensor, a heartbeat sensor, a light sensor, an infrared sensor, a brainwave sensor or a pressure sensor.

The microphone may be used in operation for measuring sound. The microphone is preferably positioned at the user side of the device. More preferably, the microphone is positioned at a head portion of the device.

The temperature sensor may be used in operation for measuring a body temperature of the user. Preferably, the temperature sensor is positioned at the user side of the device. The temperature sensor may be used for detecting a presence of a user. In an embodiment, the temperature sensor may be used to detect a presence of a body part on the cushioning or to measure a body part temperature which temperature sensor is then positioned close to or at the body part support, in particular at the hand pad.

The heartbeat sensor, for example a blood oxygen saturation sensor, may be positioned at the cushioning for measuring the heart rate on the body part.

The light sensor may be used in operation for determining a darkness of an environment. The light sensor may be used to start operation of the device. Preferably, the light sensor is positioned at a freely exposed side of the device, e.g. at a head or tail portion end face. In an embodiment, a light sensor may be used in operation for detecting a presence of the body part on the cushioning, in particular a hand on the hand pad. Then, the light sensor is positioned at the cushioning, in particular at the hand pad.

The infrared sensor may be used in operation for detecting a presence of a user. The infrared sensor is preferably positioned at a user side of the device.

The brainwave sensor for brainwave measurements is preferably positioned at a user side of the device, in particular at the head portion of the device.

The pressure sensor for detecting a presence of the body part on the cushioning is preferably positioned close to the cushioning for supporting a body part, in particular at the hand pad.

Further embodiments according to an aspect of the invention are defined by the following clauses:

1. Relaxation monitoring device (1) for monitoring a physiological characteristic of a user (P) during relaxation, comprising:
   a cushion (17) having an outer surface which provides a cushioning to support a human hand (BP), wherein when seen in a top view the cushion (17) defines an outer shape (10) of the device which outer shape is elongated along a longitudinal axis (L-L), in which a head portion (HP) and a tail portion (TP) of the outer shape are defined in which the head portion (HP) has a length along the longitudinal axis which equals a length along the longitudinal axis of the tail portion (TP);
   a housing (20) for housing components of the device, which housing is at least partially covered by the cushion (17), wherein the housing comprises an outer shell (110) which delimits an inner space (119) for containing electrical components, like a battery, a motor, an air-pump and a control unit;
   at least one sensor (31) for monitoring the psychological characteristic of the user, which at least one sensor (31) is positioned at the head portion (HP) of the outer shape of the relaxation monitoring device;
   a control unit (30) connected to the at least one sensor (31) for receiving a sensor signal from the at least one sensor (31);
   wherein the at least one sensor (31) comprises a respiratory sensor (31) for monitoring an exhaled air flow from the user, wherein at least one air passageway (310, 311, 312) is provided at the head portion (HP) at a user side (us) which is a side of the outer shape which side is in use to be directed towards the user which at least one air passageway is in fluid communication with the respiratory sensor (31) to allow the airflow flowing from an outside of the device to the respiratory sensor (31);
   wherein a centre of gravity (CG) of the relaxation monitoring device (1) is positioned in the tail portion (TP) of the outer shape, such that in starting use—when picking up the device—due to a natural tendency the relaxation monitoring device will be held by the user in a predetermined orientation, in which the head portion (HP) is directed to a face of the user and the tail portion (TP) is directed to an abdominal of the user; and wherein the elongated outer shape (10) has an outer contour (OC) which includes a concave portion which forms a hand pad (171) which concave portion is positioned at a side of the outer shape which side is in use to be directed away from the user, such that in use due to a natural tendency the at least one passageway (310, 311, 312) will be directed towards a face of the user when the user places a hand onto the hand pad and attracts the relaxation monitoring device towards the user's body.

2. Relaxation monitoring device according to clause 1, wherein the respiratory sensor (31) is a CO2 sensor (310) for measuring a CO2 concentration in an exhaled air flow from the user, wherein the CO2 sensor is a chip-shaped sensor mountable to a printed circuit board (3).

3. Relaxation monitoring device according to clauses 1 or 2, wherein the centre of gravity of the device (1) is positioned in a region in a lower half of a length of the tail portion (TP) along the longitudinal axis (L-L) which lower half is positioned adjacent to a tail portion end face (TPe).

4. Relaxation monitoring device according to any of the preceding clauses, wherein the respiratory sensor (31) is positioned in a region in an upper half of the length of the head portion (HP) along the longitudinal axis (L-L) which upper half is positioned adjacent to a head portion end face (HPe).

5. Relaxation monitoring device according to any of the preceding clauses, wherein the relaxation monitoring device comprises a battery (19), a motor, in particular a pump-unit including a motor and a pump, and a suspension (15) for suspending the motor or pump-unit inside the housing, wherein the suspension in assembly with the motor or pump unit has a centre of gravity which is positioned in the tail portion (TP) of the relaxation monitoring device.

6. Relaxation monitoring device according to any of the preceding clauses, wherein the relaxation monitoring device comprises a light emitting element, like a control panel (18) or LED (32), which is positioned at the hand pad side of the relaxation monitoring device.

7. Relaxation monitoring device according to any of the preceding clauses, wherein the at least one air passageway (310, 311, 312) extends from the outer surface of the cushion (17) through the housing (11) to the respiratory sensor (31), wherein the relaxation monitoring device comprises a group of at least two air passageway (310, 311) positioned along the outer contour, wherein in particular each air passageway has a diameter of at least 5 mm.

8. Relaxation monitoring device according to any of the preceding clauses, wherein the relaxation monitoring device is a hand-pillow for supporting a human hand, which hand-pillow is sized, in particular having a total volume of at most 10 L.

9. Relaxation monitoring device according to any of the preceding clauses, wherein the side of the relaxation monitoring device which is in use to be directed towards the user, the user side, is convex shaped, wherein in particular the outer shape of the relaxation monitoring device has a kidney-shape including the concave portion at the hand pad side and the convex portion at the user side.

10. Relaxation monitoring device according to any of the preceding clauses comprising a stimulator (12), wherein the stimulator (12) is configured to provide a haptic stimulus, wherein the stimulator is positioned under the hand pad (11) for transferring haptic stimuli via the hand pad to the user's hand.

11. Relaxation monitoring device according to clause 10, wherein the stimulator (12) comprises an air chamber which is inflatable by a pump-unit, which air chamber is connected to a pump unit for frequently inflating the chamber, wherein the air chamber is positioned below the hand pad (11) for transferring the haptic stimulus to a user's hand.

12. Relaxation monitoring device according to any of the clauses 1-9 comprising a data transfer element for controlling another electronic device, such as relaxing tools, climate control devices, alarming devices etc. based on a measurement of a physiological characteristic during relaxation.

13. Relaxation monitoring device (1) for monitoring a physiological characteristic of a user (P) during relaxation, comprising:

a cushion (17) having an outer surface which provides a cushioning to support a body part (BP), wherein the cushion (17) defines an outer shape (10) of the device which outer shape is elongated along a longitudinal axis (L-L), in which a head portion (HP) and a tail portion (TP) of the outer shape are defined in which the head portion (HP) has a length along the longitudinal axis which equals a length along the longitudinal axis of the tail portion (TP);

a housing (20) for housing components of the device, which housing is at least partially covered by the cushion (17), wherein the housing delimits an inner space (119) for containing electrical components, like a battery, a motor, an air-pump and a control unit;

at least one sensor (31) for monitoring the psychological characteristic of the user, which at least one sensor (31) is positioned at the head portion (HP) or tail portion (TP) of the outer shape of the relaxation monitoring device;

a control unit (30) connected to the at least one sensor (31) for receiving a sensor signal from the at least one sensor (31).

14. Relaxation monitoring device (1) according to clause 13, wherein a centre of gravity (CG) of the relaxation monitoring device (1) is positioned in the tail portion (TP) of the outer shape, such that in starting use—when picking up the device—due to a natural tendency the relaxation monitoring device will be held by the user in a predetermined orientation, in which the head portion (HP) is directed to a face of the user and the tail portion (TP) is directed to an abdominal of the user, such that the at least one sensor or another component, e.g. a display or speaker, is optimally positioned for operation of the relaxation monitoring device.

15. Relaxation monitoring device (1) according to clause 13 or 14, wherein the cushioning is a hand pad for supporting a hand of a user.

16. Relaxation monitoring device (1) according to clause 15, wherein the hand pad is formed by a concave portion of the elongated outer shape.

17. Relaxation monitoring device (1) according to clause 15 or 16, wherein the hand pad includes a heating pad for warming the hand of the user.

18. Relaxation monitoring device (1) according to any of the clauses 13-17, wherein a stimulator, in particular an inflatable air chamber, is positioned at the hand pad.

19. Relaxation monitoring device (1) according to any of the clauses 13-18, wherein the relaxation monitoring device includes a heating pad for warming a user which is positioned or connectable by a user at an user side of the outer shape of the device.
20. Relaxation monitoring device (1) according to any of the clauses 13-19, wherein the relaxation monitoring device comprises a control panel and/or a display which is positioned at a side other than the user side, in particular at the hand pad side.
21. Relaxation monitoring device (1) according to any of the clauses 13-20, wherein the at least one sensor is a sensor selected from a group of sensors comprising:
    a microphone for measuring sound, which microphone is preferably positioned at the user side of the device, in particular at a head portion of the device;
    a temperature sensor for measuring a body temperature of the user, in which the temperature sensor is preferably positioned at a user side of the device;
    a heartbeat sensor for measuring a heart rate which is preferably positioned close to the cushioning for supporting a body part, in particular at the hand pad;
    a light sensor for determining a darkness of an environment;
    an infrared sensor for detecting a presence of a user, in which the infrared sensor is preferably positioned at a user side of the device;
    brainwave sensor for brainwave measurements which brainwave sensor is preferably positioned at a user side of the device, in particular at the head portion of the device
    a temperature sensor for detecting a presence of a body part on the cushioning which temperature sensor is preferably positioned close to the cushioning for supporting a body part, in particular the hand pad;
    a pressure sensor for detecting a presence of the body part on the cushioning which pressure sensor is preferably positioned close to the cushioning for supporting a body part, in particular at the hand pad;
    a light sensor for detecting a presence of the body part on the cushioning, in particular a hand on the hand pad.
22. Monitoring method for monitoring a person during relaxation by using a relaxation monitoring device, wherein the method comprises the steps of:
    providing a relaxation monitoring device according to any of the preceding clauses;
    picking up the relaxation monitoring device by placing a hand onto a hand pad of the relaxation monitoring device;
    bringing the relaxation monitoring device in an operational orientation by attracting the relaxation monitoring device towards a person's body;
23. Use of the relaxation monitoring device as a sleep inducing device for guiding a user in falling asleep and/or to guide the user during a sleep session to manage a sleep pattern.
24. Use of the relaxation monitoring device for operating connected devices e.g. for operating a massage chair or for climate control of a room.

BRIEF DESCRIPTION OF DRAWINGS

The invention will be explained in more detail with reference to the appended drawings. The drawings show practical embodiments according to the invention, which may not be interpreted as limiting the scope of the invention. Specific features may also be considered apart from the shown embodiments and may be taken into account in a broader context as a delimiting feature, not only for the shown embodiment but as a common feature for all embodiments falling within the scope of the appended claims. In the figures:

DETAILED DESCRIPTION

Figure 1:
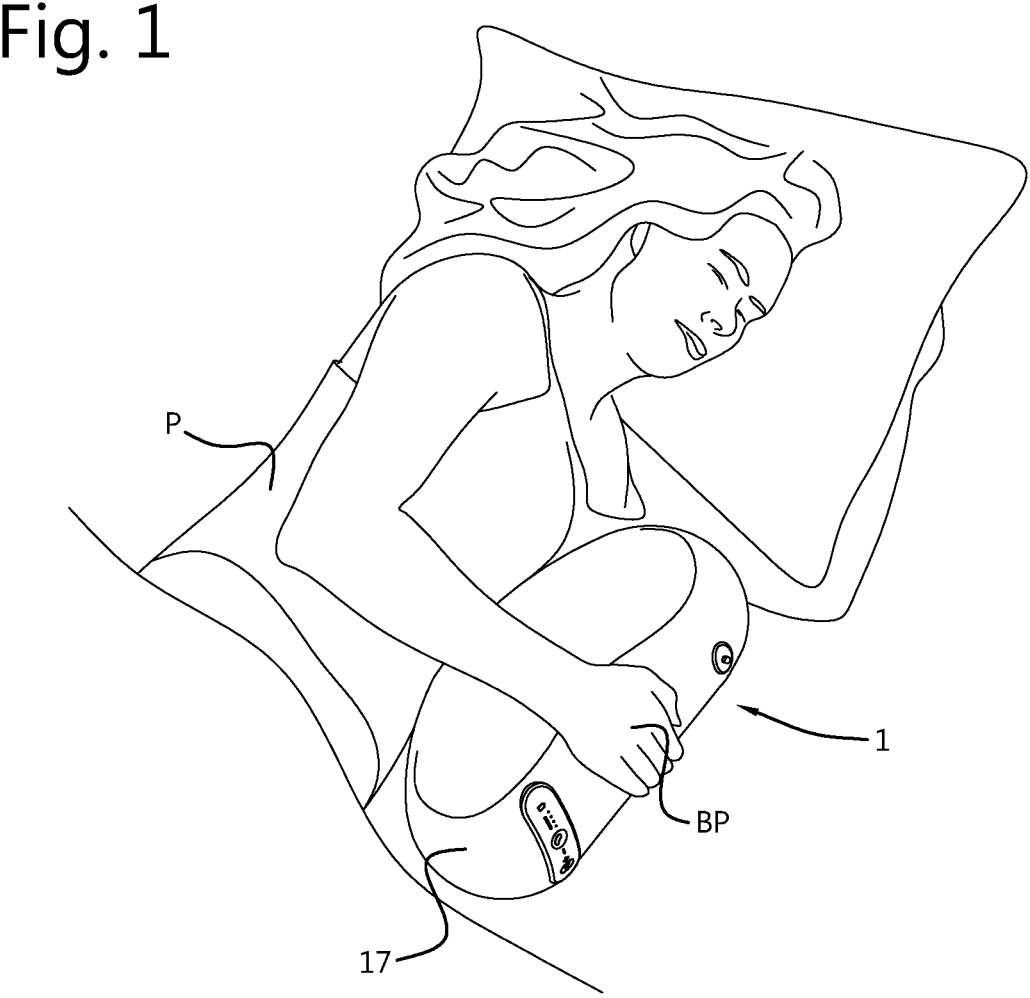
FIG. 1 schematically shows a user lying in bed while spooning and holding an embodiment of a haptic respiration simulator according to the invention.

With reference to FIG. 1 a user, person P, is shown while lying in bed. The person P spoons a haptic respiration simulator 1 and touches the haptic respiration simulator 1 with a body part BP, here a hand. The haptic respiration simulator 1 is able to simulate a respiration by alternatingly contracting and expanding as will be explained in the below. The person P is able to sense said simulated respiration with hand BP. Research shows that when the simulated respiration is relatively slow compared to an average respiration of a person P, this has a relaxing effect on the user P.

For example, the haptic respiration device 1 may be used to relax a person P, e.g. during a busy day and while sitting in a comfortable chair (not shown), by holding the haptic respiration device 1, and sensing the comforting simulated respiration.

For example, the haptic respiration device may be used to guide a person towards a sleep phase by relaxing the user. More specifically, by inducing changes in the respiration frequency of the person P, the person P may be guided towards a state of (initial) sleep.

As is visible in FIG. 1, the haptic respiration device 1 may be formed as a peanut-shaped pillow, having a soft outer skin 17, e.g. comprising a layer of foam material. As will become more clear from the below, the soft outer skin 17 may function as a third suspension to dampen noise originating from operation of a pump unit, which pump unit is positioned inside the haptic respiration simulator 1. This third suspension layer helps to silence the haptic respiration simulator 1 and makes it easier for person P to fall asleep and/or to relax, besides making the haptic respiration simulator more appealing to use for a user P.

Figure 2:
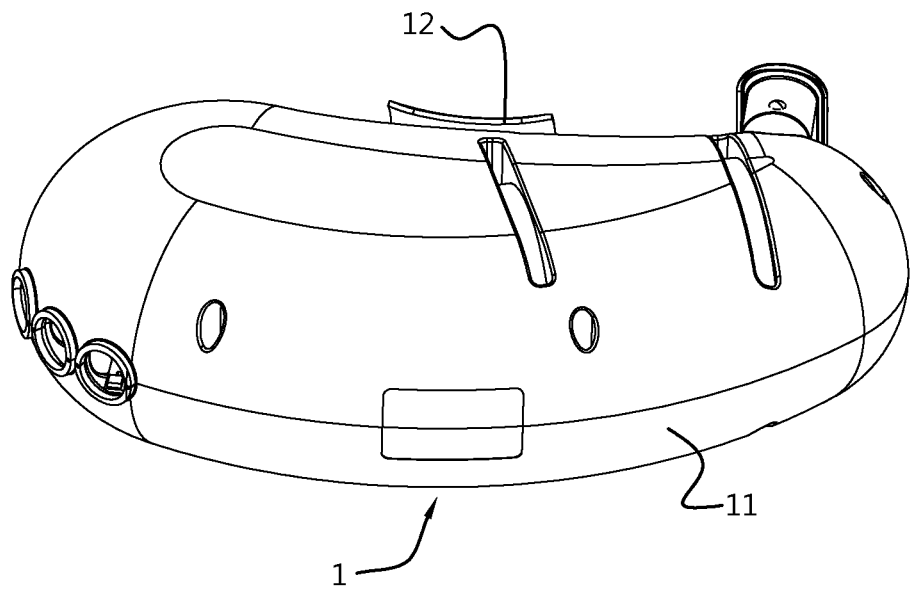
FIG. 2 schematically shows a housing of the haptic respiration simulator of FIG. 1.

Turning to FIG. 2, the haptic respiration simulator 1 is here shown without user, and without the outer soft skin. Shown here is the outer housing 11 for housing components of the haptic respiration simulator, as well as inflatable air chamber 12. As is visible, the inflatable air chamber 12 is positioned outside or external of the outer housing 11. The inflatable air chamber 12 is in fluid communication with a pump unit arranged inside the outer housing and not visible in FIG. 2. The inflatable air chamber 12 is configured to simulate a respiration by repeated inflation (expansion) and deflation (contraction) of the inflatable air chamber 12. This inflation and deflation of the inflatable air chamber 12 can be sensed by a user through the outer skin of the haptic respiration simulator 1.

The housing 11 may be made of a plastic material, that is preferably formed by an injection moulding process.

Air is pumped in the inflatable air chamber 12 by a pump unit. Preferably, the inflatable air chamber 12 is of a semi-permeable material, e.g. a material having small holes in it, so that the air chamber 12 automatically deflates, without the need for an air suction unit to deflate the inflatable air chamber 12. This decreases the amount of components needed. However, an air suction unit may be part of the haptic respiration simulator, e.g. to provide a better control over the respiration simulation.

Figure 3:
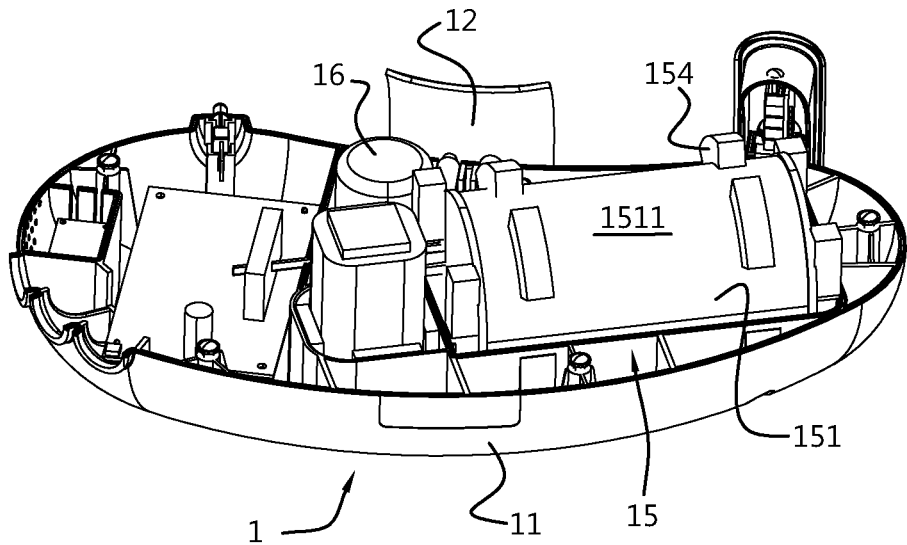
FIG. 3 schematically shows the inside of the housing of FIG. 2.

Turning now to FIG. 3, the inside of the housing 11 is visible, as well as the inflatable air chamber 12 which is arranged outside of the housing 11. The housing 11 houses several components of haptic respiration simulator 1, amongst which a pump unit, not visible, and the pump unit suspension system 15, of which tubular casing or tubular core 151 is well visible in FIG. 3. Hence, the pump unit suspension system 15, the pump unit, and the tubular casing 151 are positioned inside the housing 11. The pump unit is contained inside tubular casing 151 and therefore hidden from sight in FIG. 3. Also visible in FIG. 3 is outer suspension 154, here in the form of foam material, positioned at the outside of a closed circumferential wall 1511 of the tubular casing, along different locations thereof. The foam material, here in the form of blocks, suspend the tubular casing 151 with respect to the housing 11 and is placed between the tubular casing 151 and the housing 11, inside housing 11.

However, the outer suspension 154 may also comprise a layer of suspension material, fully or partly surrounding the tubular casing 151. For example, the layer of suspension material may comprise foam.

Also visible in FIG. 3 is a (second) accumulator 16, positioned inside the housing 11 and outside of the tubular casing 151. The second accumulator 16 will be described in more detail below, with reference to FIG. 6.

Figure 4:
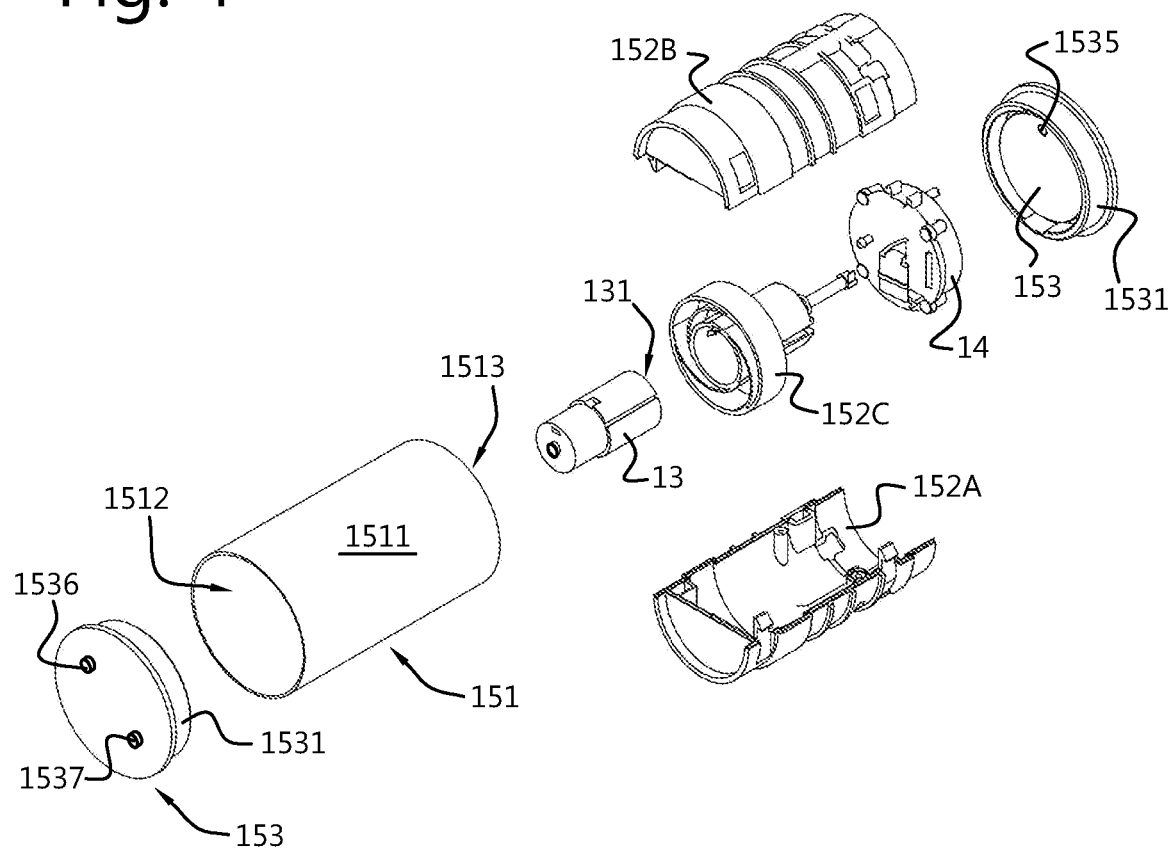
FIG. 4 schematically shows a first embodiment of the pump unit and the pump unit suspension system according to the invention.

Turning to FIG. 4, an exploded view of components of the pump unit suspension system is shown. The tubular casing 151 is again shown, as well as components of the haptic respiration simulator associated with the tubular casing 151. A pair of end caps 153 is positioned at ends 1512, 1513 of the tubular casing 151, to seal the tubular casing 151. A pump unit 13 is positioned inside the tubular casing 151, and thus inside the housing 11. Pump unit 13 is in fluid communication with accumulator 14 and suspended with respect to the tubular casing 151 via inner suspension 152A, 152B, 152C. Also accumulator 14 and inner suspension 152A, 152B, 152C are positioned inside tubular casing 151 when the haptic respiration simulator is assembled.

The tubular casing 151 has an inner volume 1514, in which the pump unit 13 is received. A circumferential wall 1511 of the tubular casing 151 is substantially closed, so as to prevent at least a part of the sound waves that result from an operation of the pump unit 13 to transfer outside of the tubular casing 151.

In the shown embodiment, the tubular casing 151 is round. The tubular casing 151 may however also be cylindrical, rectangular, triangular, or square, possibly with rounded edges. The tubular casing 151 may in principle have any shape.

The tubular casing 151 is here hollow, and has open ends 1512, 1513. The circumferential wall 1511 is closed, i.e. has a continuous circumference without any holes, apertures or cut-outs to optimally prevent the escape of sound waves in a radial direction. The circumferential wall 1511 may be made of steel, or other dense materials, e.g. metals with a density higher than steel. The circumferential wall 1511 is here thick-walled, having a thickness of at least 1 mm, e.g. 1.5 mm, here at least 2.0 mm.

The pump unit 13, housed inside the tubular casing 151 when the haptic respiration simulator is assembled, is in fluid communication with the inflatable air chamber, for pumping air into the inflatable air chamber. Preferably, the pump unit 13 is an axially operated pump unit, that provides pulses of air via an outlet 131 of the pump unit 13. Although the pump unit 13 is in fluid communication with the inflatable air chamber, components of the haptic respiration simulator may be placed in between the inflatable air chamber and the pump unit 13 (when seen in a flow direction from the pump unit 13 to the inflatable air chamber).

The accumulator 14 is an example of such a component that may be placed in between the inflatable air chamber and the pump unit 13. The accumulator 14 is in fluid connection with the outlet 131 of the pump unit 13, and with the inlet of the inflatable air chamber (either directly, when there is only a single, first, accumulator, or indirectly, when there is a second accumulator. This will be explained in the below). The accumulator 14 is here positioned inside the tubular casing 151, when the haptic respiration simulator is assembled.

The end caps 153 are here made of a resilient material, e.g. silicon. However, the end caps 153 may also be made of a relatively rigid material, e.g. a moulded plastic, or a metal such as steel. The end caps 153 or one of the end caps 153 may be integrated with the circumferential wall 1511 of the tubular casing 151 when the tubular casing 151 and the end caps 153 are made of the same material. When the end caps 153 are made of a relatively rigid material, but of a different material than the tubular casing 151, preferably resilient material is positioned between the end caps 153 and the tubular casing 151, such that a transfer of noise-inducing vibrations from the tubular casing 151 to the rigid end cap 153 is prevented.

Visible in one of the end caps 153 is therefore a passage hole 1535, e.g. for passage of an air tube that fluidly connects the accumulator 14 with the inflatable air chamber.

Preferably, as shown, the end caps 153 are substantially solid and completely seal the tubular casing 151, i.e. preferably the end caps do not comprise any holes through which noise may escape.

However, the pump unit 13 should also be able to suck in fresh air for pumping it into the inflatable air chamber. Visible in the other of the end caps 153, are therefore suction holes 1536, 1537, through which the pump unit 13 may receive air, e.g. via air suction tubes. When an air tube is placed in the suction hole 1536, 1537, the amount of noise that can transfer outside of the tubular casing 151 may be significantly reduced compared to when the suction hole is left open.

The inner suspension 152 for suspending the pump unit 13 with respect to the tubular casing 151 comprises here suspension member 152C and suspension shell 152A, 152B. The suspension member 152C and especially suspension shell 152A, 152B are preferably made of a material that is more resilient that the tubular casing 151. For example, when the tubular casing 151 is made of a metal, the suspension shell 152A, 152B may be made of a plastic material that is injection moulded. When the pump unit suspension system 15 is assembled, suspension shell 152A, 152B encapsulates pump unit 13, accumulator 14, and suspension member 152C.

While suspension member 152C may reduce the amount of air vibrations that result from operating the pump unit 13, by suspending pump unit 13 about a central position inside tubular casing 151, suspension shell 152A, 152B may prevent that air vibrations which do result from operation of the pump unit 13 are not, or only partially, transferred outside of tubular casing 151.

Figure 5A:
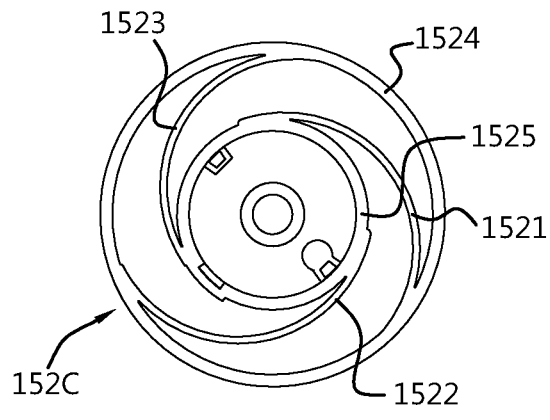
FIGS. 5a and 5b schematically show a more detailed view of the inner suspension as shown in FIG. 4.
Figure 5B:
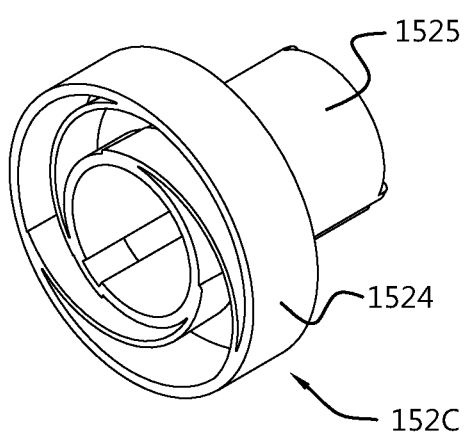

The suspension member 152C of inner suspension 152 is shown in some more detail in FIGS. 5A and 5B. As shown, the suspension member 152C here comprises an inner circumferential wall 1525, an outer circumferential wall 1524, and at least three resilient elements 1521, 1522, 1523. The inner circumferential wall 1525 is for receiving the pump unit therein, and is connected to the outer circumferential wall 1524 via resilient elements 1521, 1522, 1523. The number of resilient elements 1521, 1522, 1523 here equals three, but of course more or less resilient elements may alternatively be chosen. However, to optimally stabilize and suspend the pump unit, at least three resilient elements are recommended. The resilient elements 1521, 1522, 1523 are arranged at different positions along the circumference of the pump unit, when the pump unit is placed inside the inner circumferential wall 1525 of the suspension member 152C, and suspend the pump unit about a central position in the internal volume of the tubular casing.

Outer circumferential wall 1524 of suspension member 152C is arranged inside and against suspension shell 152A, 152B. Also accumulator 14 is arranged inside suspension shell 152A, 152C.

Returning to FIG. 4, when the haptic respiration simulator is assembled, an outside of the pump unit 13 may be positioned inside the suspension shell 152A, 152B, and inside suspension member 152C, against an inside of the inner circumferential wall 1525 of suspension member 152C. The end caps 153 are positioned at open ends 1512, 1513 of the tubular casing 151, with inwardly protruding walls 1531 of the end caps 153 being positioned against an inside of the closed circumferential wall 1511 of the tubular casing. Preferably, these inwardly protruding walls 1531 slightly exceed the inner diameter of the tubular casing 151, to tightly fit the end cap 153 in the tubular casing 151. The outside of the suspension shell 152A, 152B may then positioned against the inside of the inwardly protruding walls 1531 of the end caps 153, inside tubular casing 151, between the pump unit 13 and the tubular casing 151.

Outer circumferential wall 1524 of suspension member 152C and/or accumulator 14 may alternatively be placed against circumferential wall 1511 of the tubular casing 151 or against the inwardly protruding wall 1531 of end caps 153 when assembled, e.g. when suspension shell 152A, 152B is absent.

Figure 6:
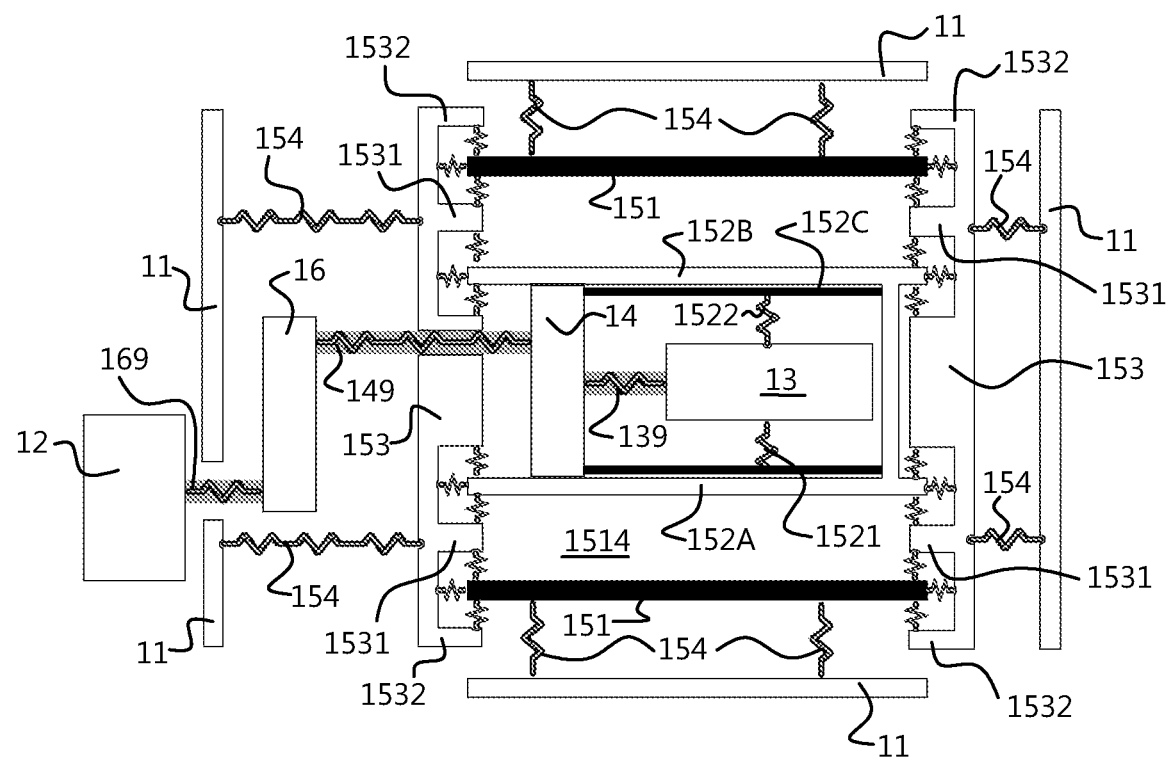
FIG. 6 schematically shows the layout of the pump unit suspension system of FIG. 4, arranged inside the housing.

FIG. 6 more schematically shows the pump unit suspension system 15 in an assembled state. All components of the pump unit suspension system 15 are here positioned inside housing 11, the only component of the haptic respiration simulator arranged outside of the housing 11 being the air chamber 12. However, as explained in the above, other components of the haptic respiration simulator, such as a foam cover, may also be positioned outside the housing 11. Positioned inside the housing 11 is a pump unit 13. When operated, the pump unit 13 produces noise. As the object of the haptic respiration simulator is to relax a user, this noise is disadvantageous, and the pump suspension unit 15 is provided to reduce the noise that originates from operating the pump unit 13, such that only a part of the noise is hearable by a user. For example, the pump unit 13 may generate a noise level of more than 50 dBA when operated, the pump unit suspension system being aimed at reducing that noise level with at least 10 dBA, e.g. at least 13 dBA, preferably with up to 20 dBA or more to an overall noise level of 40 dBA or below.

Therefore, the pump unit suspension system 15 comprises a first accumulator 14 and, optionally, a second accumulator 16. Here, both accumulators 14, 16 are positioned inside the housing, with the first accumulator 14 being positioned inside an internal volume 1514 of the tubular casing 151, and the second accumulator 16 being positioned outside of the internal volume 1514 of the tubular casing 151. The pump unit 13 may provide a pulse-wise output of air, wherein these pulses of air may produce noise. To reduce this noise, the one or more accumulators 14, 16 are provided. They each store a volume of air in an internal volume thereof, and therefore smoothen the airflow through air tubes 131, 141, 161 from a pulse-wise character when the air leaves the air pump 13 to a more constant air stream when it enters the inflatable air chamber 12.

When seen in flow direction, the first accumulator 14 is positioned in between the pump unit 13 and the second accumulator 16, while being in fluid communication with the air chamber 12. When seen in flow direction, the second accumulator 16 is positioned in between the first accumulator 14 and the air chamber 12, while being in fluid communication with the air pump 13.

As indicated, air tubes 139, 149, 169 between the pump unit 13, the accumulators 14, 16 and the air chamber 12 may be made of a resilient material, to dampen, reduce or prevent the amount of noise produced inside these tubes 139, 149, 169.

Although here two accumulators 14, 16 are present, the haptic respiration simulator may alternatively comprise one accumulator 14, no accumulator, or more than two accumulators.

Preferably, each of the accumulators 14, 16, if present, is positioned inside housing 11. One or more of them may additionally be positioned inside tubular casing 151, as here shown, but this is not necessary. The accumulator or accumulators may also be positioned outside of the tubular casing 151.

Positioned between the housing 11 and the tubular casing 151 is an outer suspension 154. This outer suspension 154 is here also positioned between end caps 153 and housing 11. The outer suspension 154 is here very schematically represented, and may be any type of suspension that prevents a contact between the housing 11 and tubular casing 151.

Further visible in FIG. 6 is tubular casing 151, sealed by end caps 153. The end caps 153 each have a double-walled circumferential wall, comprising an outer wall 1532 positioned at the outside of the tubular casing 151 and an inner wall 1531 positioned at the inside of the tubular casing 151. The end caps 153 may be made of a resilient material, or may be suspended with respect to the tubular casing 151. Preferably, no sound waves can be transferred from the tubular casing 151 to the end caps 153.

Positioned inside the tubular casing 151 is the pump unit 13 and the inner suspension 152A, 152B, 152C. The inner suspension 152A, 152B, 152C suspends the pump unit 13 with respect to the tubular casing 151, and here comprises suspension shell 152A, 152B and suspension member 152C. The suspension member 152C comprises resilient elements 1521, 1522. Inner circumferential wall 1531 of end caps 153 may prevent a physical contact between the suspension shell 152A, 152B and the tubular casing 151, to prevent sound waves to be transferred from the suspension shell 152A, 152B to the tubular casing 151.

Figure 7:
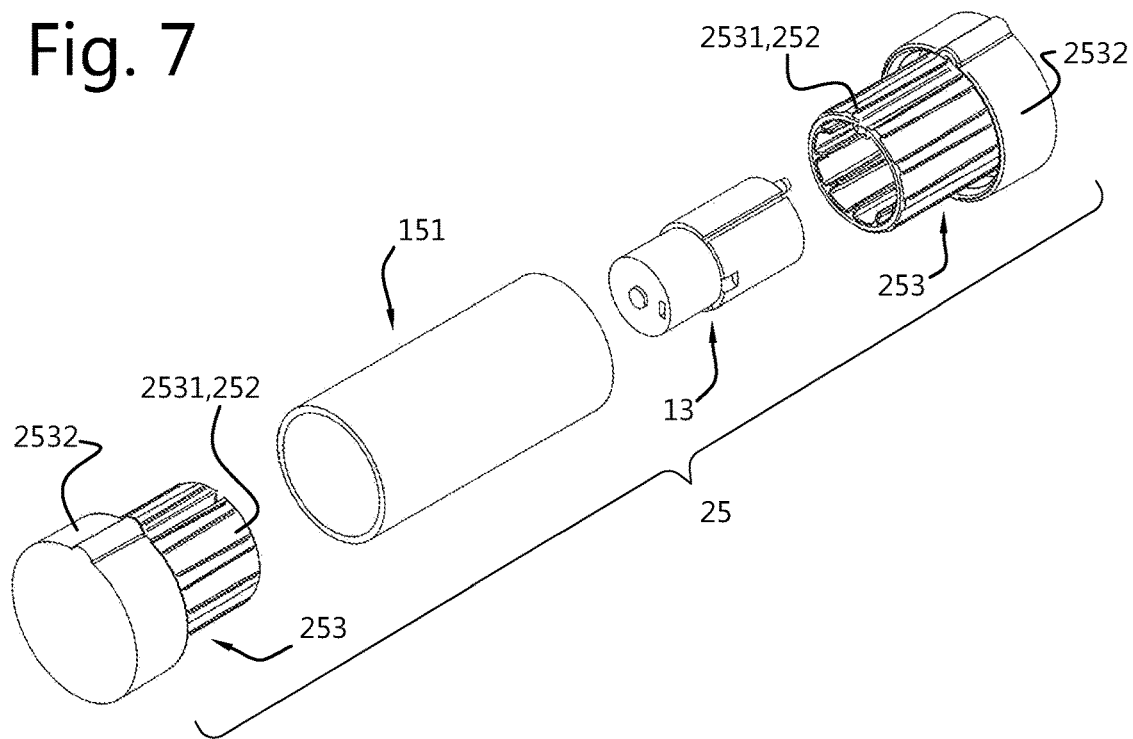
FIG. 7 schematically shows a second embodiment of a pump unit and a pump unit suspension system according to the invention.
Figure 8:
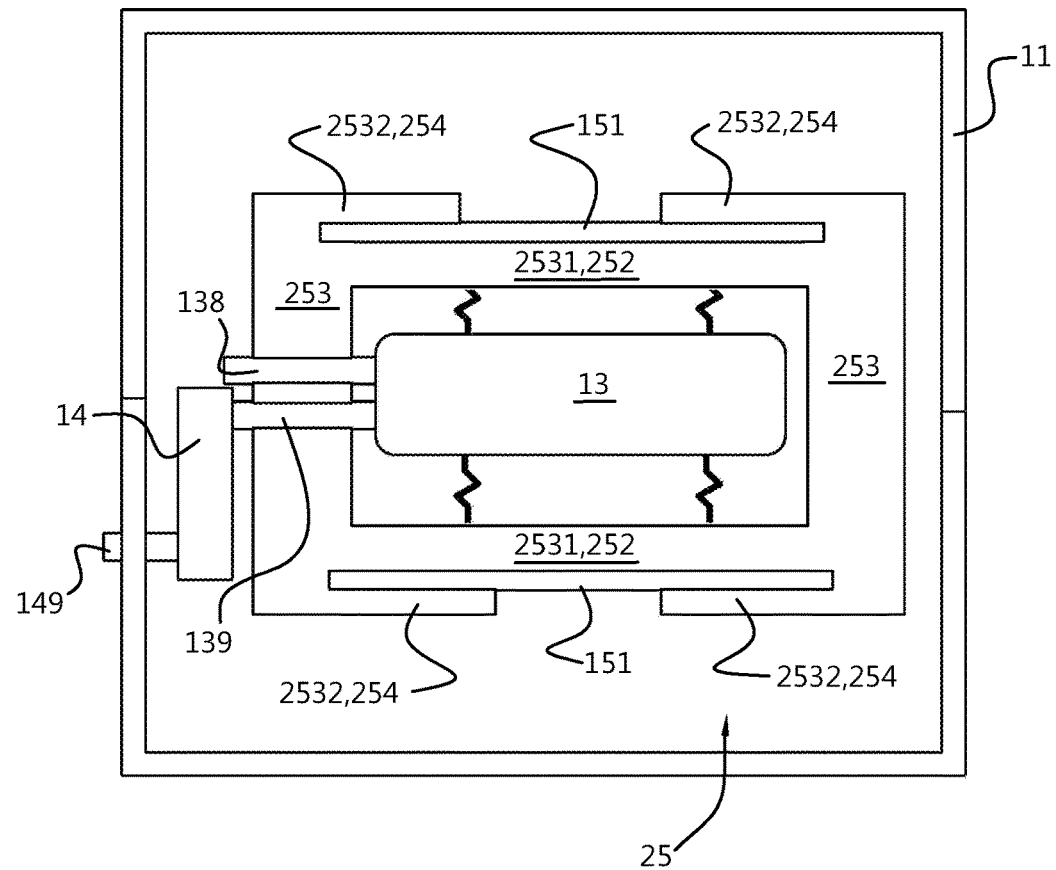
FIG. 8 schematically shows the layout of the pump unit suspension system of FIG. 7, arranged inside the housing.
Figure 9:
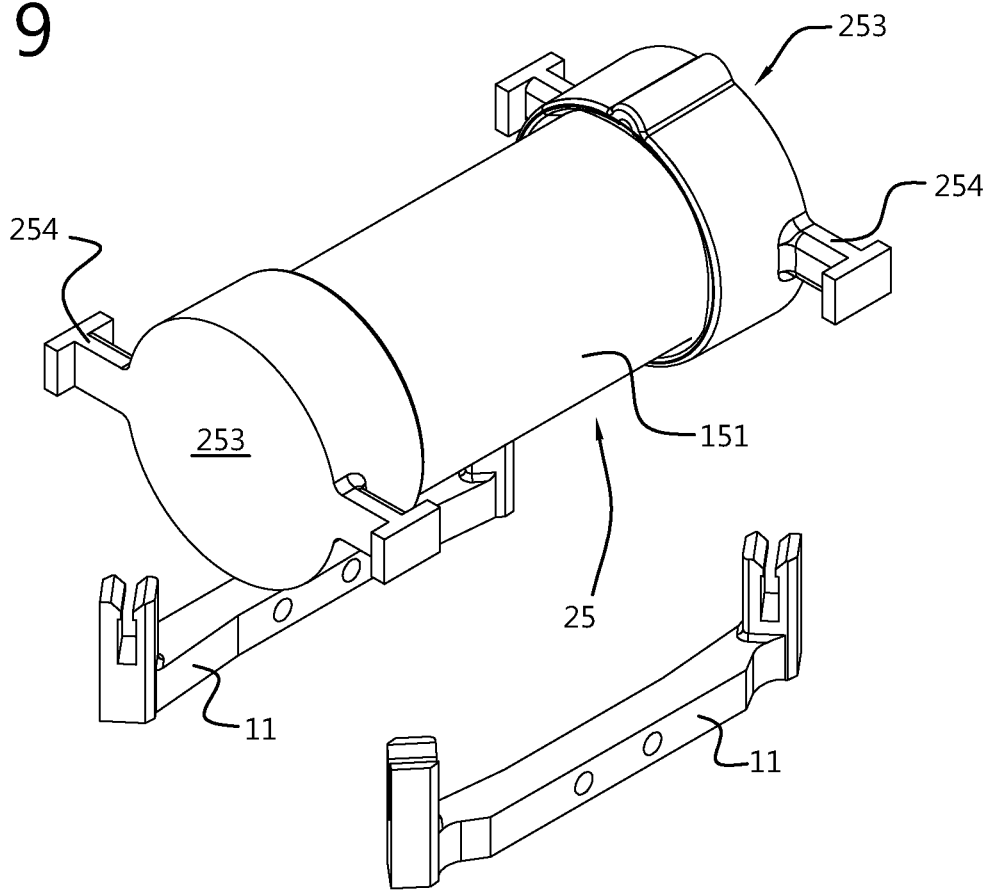
FIG. 9 schematically shows the embodiment of FIG. 7 in an assembled state a pump unit suspension system according to the invention.

An alternative embodiment of pump suspension system 25 is shown with reference to FIGS. 7-9. Shown in FIG. 7 are a pump unit 13, inner suspension 252, tubular casing 151, and end caps 253. In this embodiment, the end caps 253 have a double-walled circumferential wall with inner wall 2531 and outer wall 2532 that protrude towards the pump unit 13 when the pump unit suspension system 25 is assembled. The inner wall 2531 of the end cap 253 here functions as inner suspension 252. That is, the inner suspension 252 is integrated with the end cap 253. Each of the inner walls 2531 has a length equal to approximately half the length of the tubular casing 151, such that the inner walls 2531 touch each other when the end caps 253 are placed on the tubular casing 151. In the present embodiment, the end caps 253, and also the inner suspension 252, are made of a resilient material, e.g. silicon, and surround the pump unit 13, in both circumferential and axial direction.

Whereas FIG. 7 shows an exploded view of the pump unit 13, end caps 253 and tubular casing 151, FIG. 9 shows these components in an assembled state. From FIG. 9, it follows that the inner wall 2531 of the double-walled circumferential wall may be arranged against an inner side of the tubular casing 151, while an outer wall 2532 of the double-walled circumferential wall may be arranged against an outer side of the tubular casing 151. As further visible from FIG. 8, the outer wall 2532 of the end cap 253 may function as outer suspension 254 of pump unit suspension system 25, suspending the tubular casing 151 with respect to the housing 11.

Another schematic representation of this second embodiment is provided in FIG. 8. It is shown here how the end caps 253 comprise a double-walled circumferential wall, wherein an inner wall 2531 of the double-walled wall forms the inner suspension 252 of the pump unit suspension system 25, while an outer wall 2532 of the double-walled wall forms the outer suspension 254 of the pump unit suspension system 25.

Further visible are tubular casing 151, arranged around pump unit 13 and inside housing 11, an air tube 139 between pump unit 13 and accumulator 14, and an air suction tube 138 for providing fresh air to pump unit 13 even when it is fully surrounded by components of the pump unit suspension system.

To allow the pump unit 13 to obtain air more easily, one or more breathing holes may additionally be provided in the end caps 153.

Figure 10:
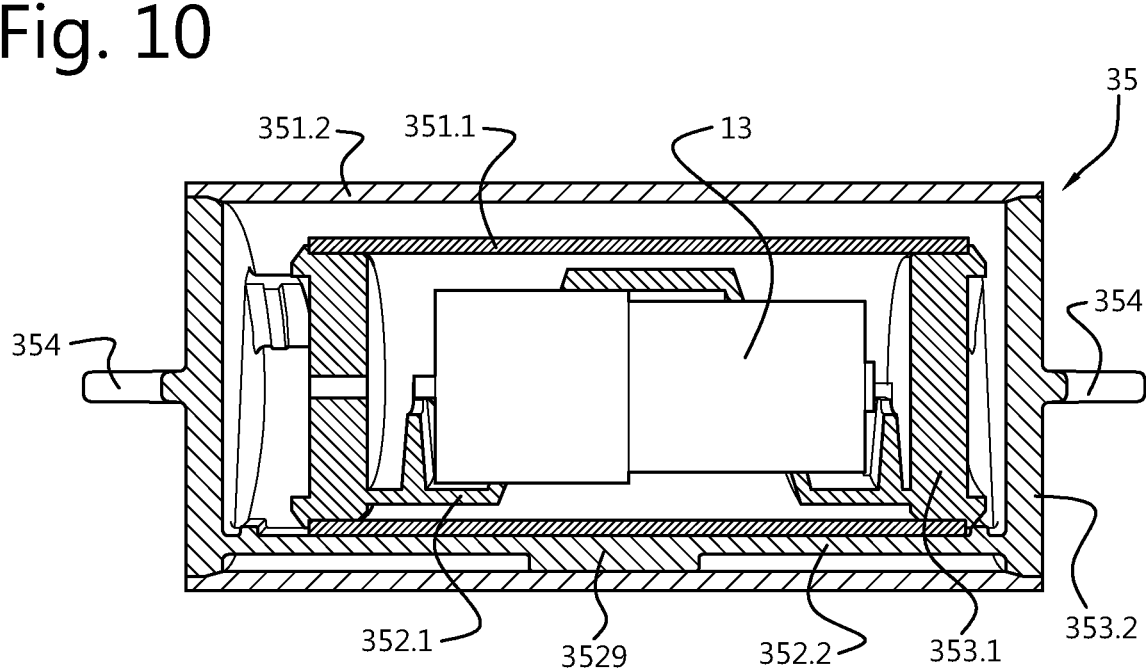
FIG. 10-12 show a third embodiment of the pump unit suspension system according to the invention, wherein a pair of end caps is integrated with and inner suspension.

FIG. 10 shows in a cross-sectional view a third embodiment of a pump unit suspension system 35 according to the invention. The pump unit suspension system 35 of this third embodiment comprises a double arrangement of the pump unit suspension system in the first and second embodiment. The pump unit suspension system 35 comprises a first and second tubular casing 351.1, 351.2, a first and second inner suspension 352.1, 352.2, a first and second pair of end caps 353.1, 353.2. The double arrangement of the pump unit suspension system is beneficial in obtaining a lightweight suspension which complies to a required noise reduction. In comparison with the first embodiment, the double arrangement is beneficial in that the second arrangement introduces a next acoustic decoupling. In addition, a total weight of the first and second tubular casing may be less than a weight of only the first tubular casing 151 due to a reduction of wall thickness.

FIGS. 11-15 show successive steps of assembling a pump unit 13 into the pump unit suspension 35.

Figure 11:
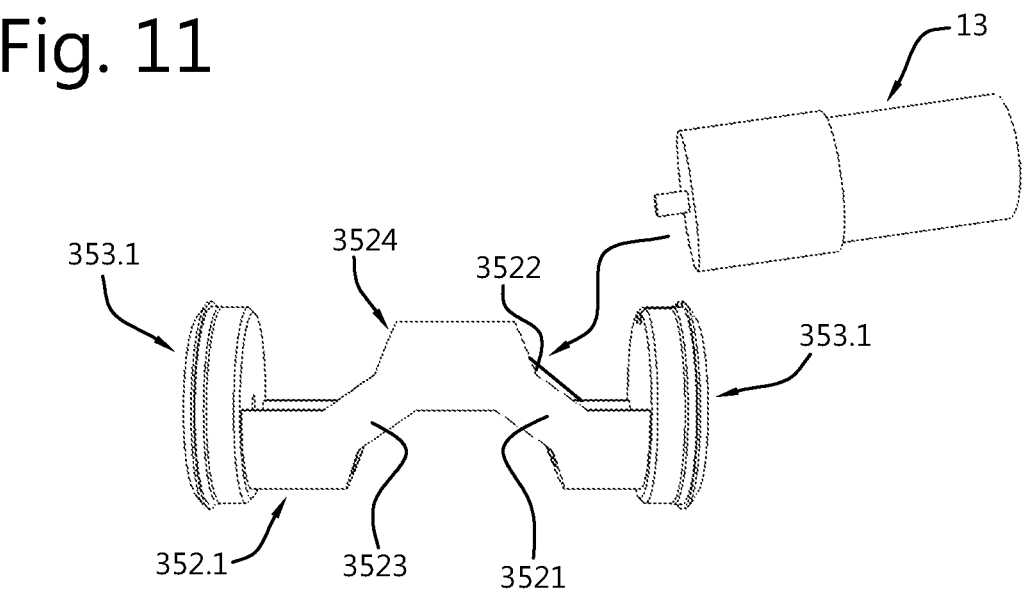

FIG. 11 shows the first inner suspension 352.1. The first inner suspension 352.1 is made of a resilient material e.g. silicon. Here, the first inner suspension 352.1 and a first pair of end caps 353.1 are incorporated to form a one-piece item. The first inner suspension 352.1 and the first pair of end caps 353.1 are integral. Preferably, the first inner suspension 352.1 and the first pair of end caps 353.1 are made of a single material. However, it is conceivable to integrate the first inner suspension and the first pair of end caps being made of different materials. For example, a first pair end caps 353.1 with integrated first inner suspension may be made using a 2K injection moulding process, wherein two different materials may be used to produce the item.

The first inner suspension 352.1 is cylindrically shaped. The first inner suspension 352.1 has an hollow inner space defined by a circumferential wall for receiving the pump unit 13. The hollow inner space is laterally open for receiving the pump unit 13 from aside as indicated by the arrows. The circumferential wall has an inner circumferential wall for receiving the pump unit therein. As indicated by the arrows, the pump unit 13 is insertable through an open region of the circumferential wall to be installed in the inner space. The resilient material of the first inner suspension 352.1, which is preferably silicone material, allows the circumferential wall to be wrapped around the pump unit 13. Here, the first inner suspension 352.1 has a circumferential wall which is open at a middle region and open at an opposite lateral side at the at least one end region. The pump unit 13 is inserted into the hollow inner space through the opening at an end region.

The circumferential wall includes at least one bridge portion in between neighbouring openings. Each bridge portion forms a resilient element 3521, 3522 for suspending the pump unit 13. Here, the first inner suspension 352.1 includes four resilient members. A pair of resilient members 3521, 3522 is positioned at a proximal end of the pump unit 13 and a pair of resilient members 3523, 3524 is positioned at a distal end of the pump unit 13.

Figure 12:
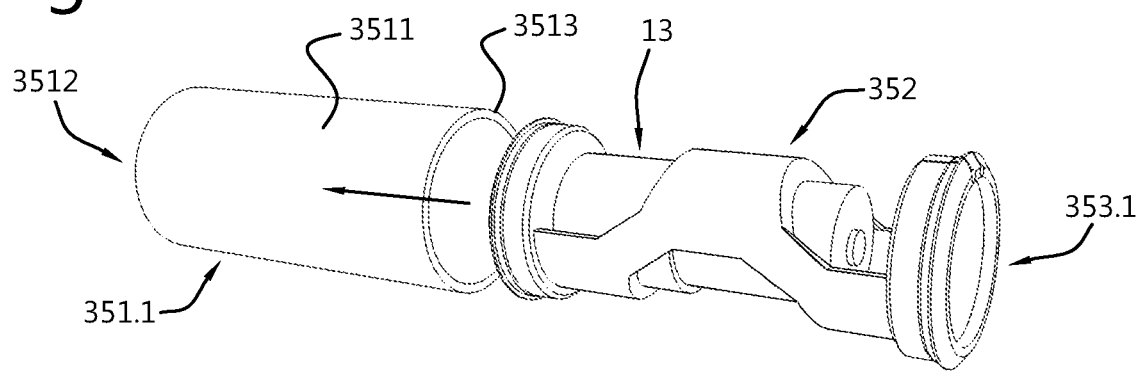
Figure 13:
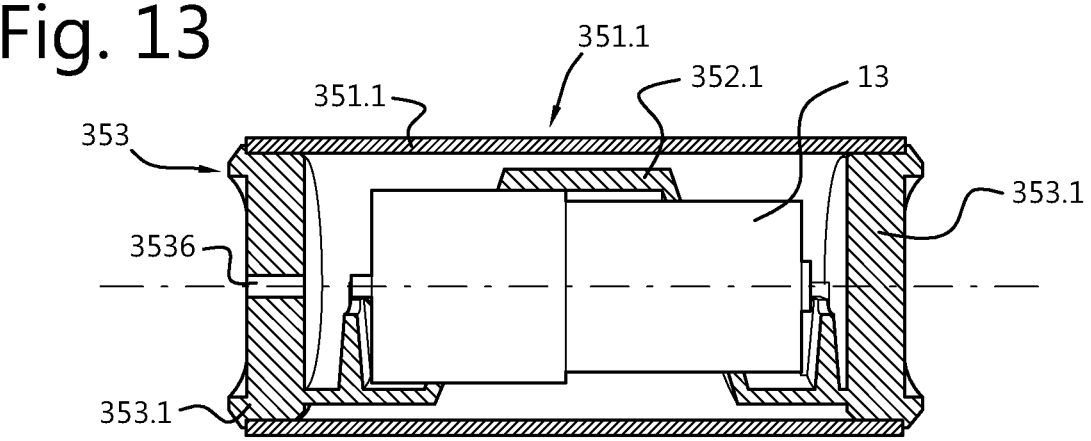
FIG. 13-18 show an embodiment, wherein the pump unit suspension system comprises a double set of inner suspensions, pair of end caps and tubular casing.

FIGS. 12 and 13 show a next step of the assembly of the pump unit 13 in the pump unit suspension system 35. As indicated by the arrow in FIG. 12, a subassembly of the pump unit 13 being received in the inner space of the first inner suspension 352 and positioned between the integrally formed first pair of end caps, is introduced in a first tubular casing 351.1. The first tubular casing 351.1 has a hollow casing body with a substantially closed circumferential wall 3511 and has a first and second open end 3512, 3513. Preferably, the first tubular casing 351.1 is made of metal, in particular steel.

In installation, the subassembly including the pump unit 13 is moved through the first tubular casing 351.1 to obtain the subassembly as shown in FIG. 13. As shown in FIG. 13, the first pair of end caps 353.1 is in abutting engagement with the ends of the casing body to close the open ends 3512, 3513. At least one of the end caps is provided with at least one through passageway 3536 for passing an air conduit or electrical wire.

Figure 14:
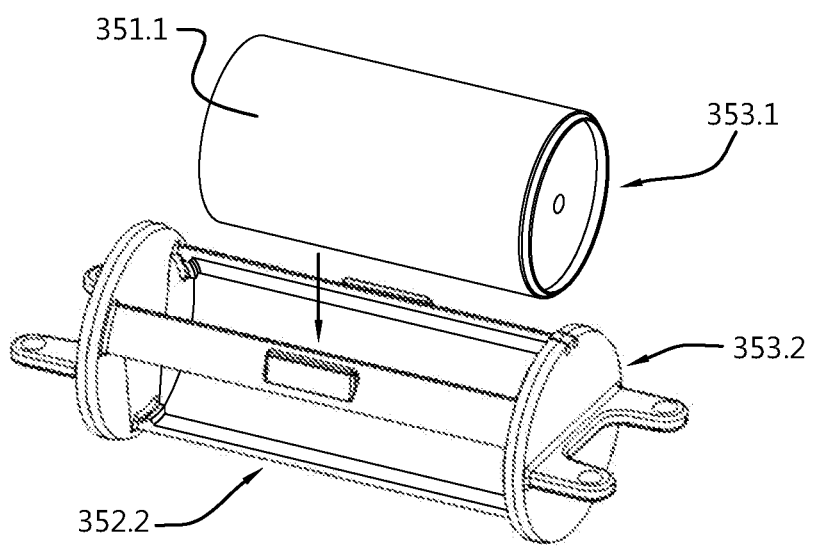
Figure 15:
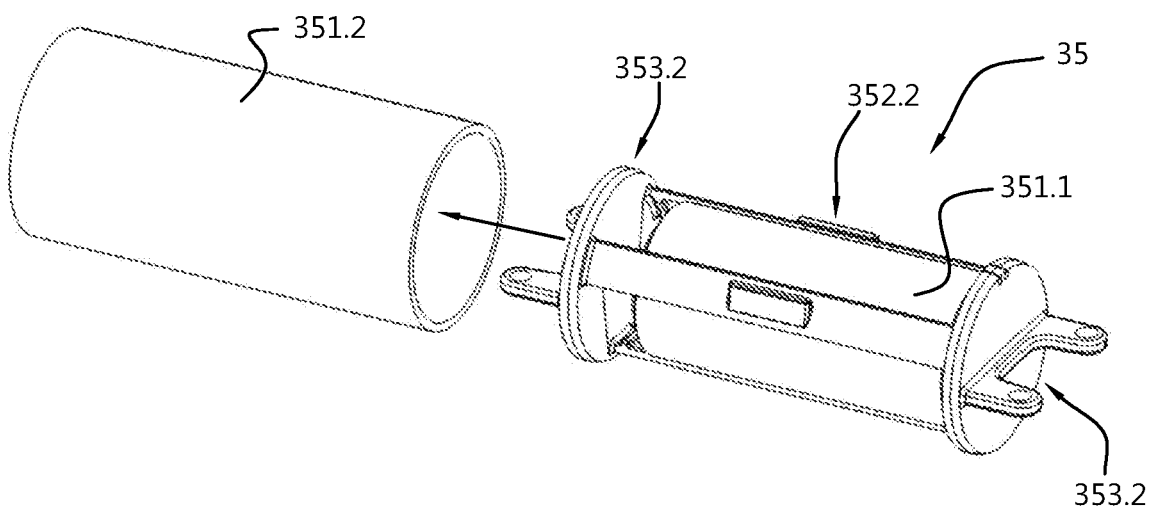

FIGS. 14 and 15 show a next step of an assembly of the pump unit suspension system 35, in which the subassembly of the first tubular casing 351.1 including the first inner suspension 352.1 with integral pair of end caps 353.1 and the pump unit 13 is received in a second inner suspension 352.2.

Figure 16:
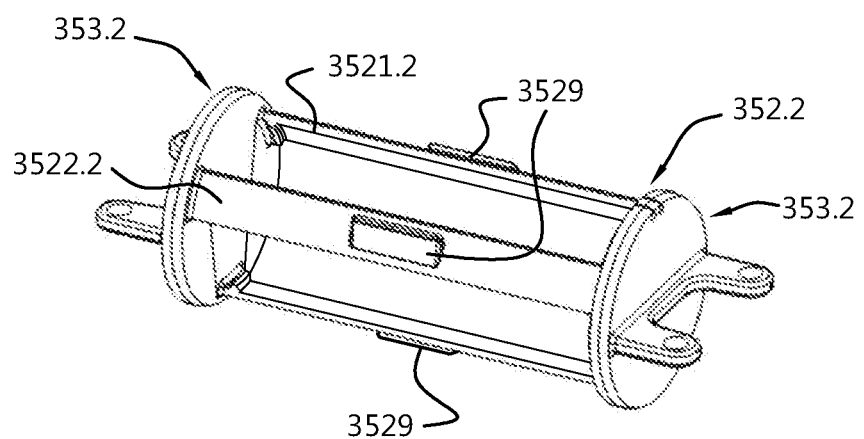

The second inner suspension 352.2 is separately shown in FIG. 16. As the first inner suspension 351.1, the second inner suspension 352.2 is made of a resilient material, preferably silicone material.

Here, the second inner suspension 352.2 is integrally formed with a second pair of end caps 353.2. The second inner suspension 352.2 has an outer circumferential wall which is formed by three longitudinally extending wall portions. An inner space is provided in between the extending wall portions for receiving the subassembly as shown in FIG. 13. Each extending wall portion forms a resilient element 3521.2 for holding the subassembly.

As shown in FIG. 15, the subassembly of the first tubular casing 351.1 as shown in FIG. 13 is received in between the extending wall portions. Subsequently, the subassembly of the second inner suspension 352.2 and the first tubular casing 351.1 is moved into the second tubular casing 351.2 to obtain the assembly as shown in FIG. 10.

An air gap is provided in between the resilient element and the second tubular casing 351.2 which provides an acoustic decoupling. Each extending wall portion has a stopper 3529. The stopper is pad-shaped and integrally formed with the wall portion. Here the stopper is positioned at a middle region. The stopper subdivides the wall portion into two resilient elements. In the assembly as shown in FIG. 10, the stopper 3529 is in abutting engagement with the second tubular casing 351.2 2 to carry a weight of the subassembly. Only locally, by the stopper 3529, the extending wall portion contacts the second tubular casing 351.2 which is beneficial in limiting a transfer of vibrations to the outside. By providing at least three stoppers around the subassembly, the subassembly can be clamped inside the second tubular casing 351.2. Due to the double arrangement including an additional acoustic decoupling, at least one of the first and second tubular casing 351.1, 351.2 may be configured with a reduced wall thickness, or another material selection, like plastic instead of steel.

Figure 17:
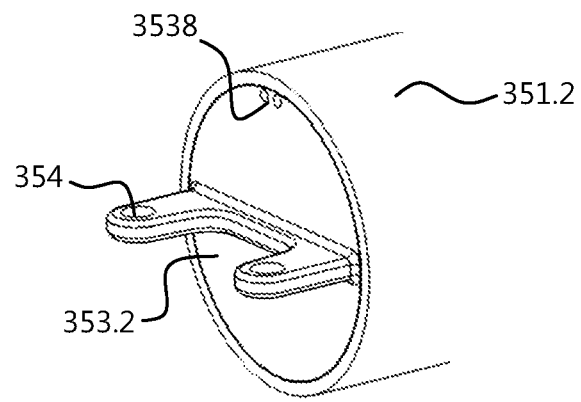
Figure 18:
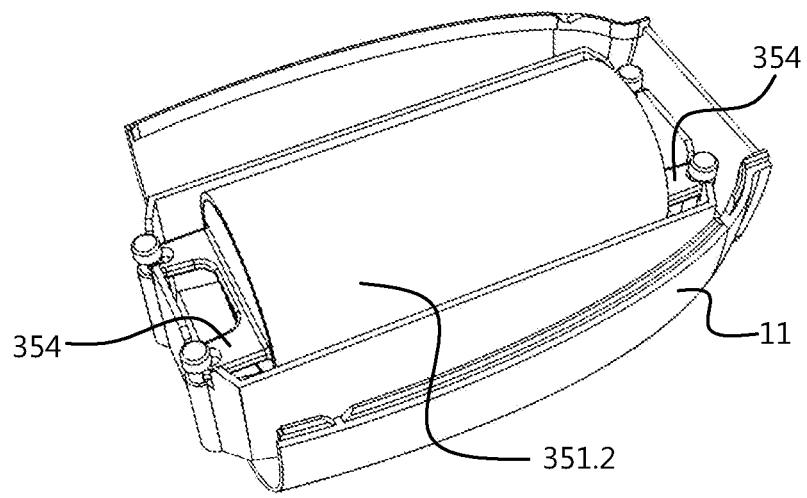

FIG. 17 is an enlarged view of an end of the second tubular casing 351.2 showing an outer suspension 354 for mounting the subassembly of both the first and second tubular casing 351.1, 351.2 to a housing 11 as it is illustrated in FIG. 18. Each end cap of the second pair of end caps 353.2 has a mounting flange forming the outer suspension 354. The mounting flange extends perpendicular to an end cap body. The mounting flange may be screwed or clamped to the housing 11. Here, the mounting flange includes at least one bore hole for screwing the subassembly to the housing 11. The mounting flange provides flexibility to the outer suspension 354. The configuration of the mounting flange is beneficial in providing a predetermined damping, because a thickness and length of the mounting flange can be designed in a dedicated manner to adapt to a particular design of the pump unit.

Identical reference numbers or alternative prefixes are used in the following drawings to indicate the same or similar features.

Figure 19:
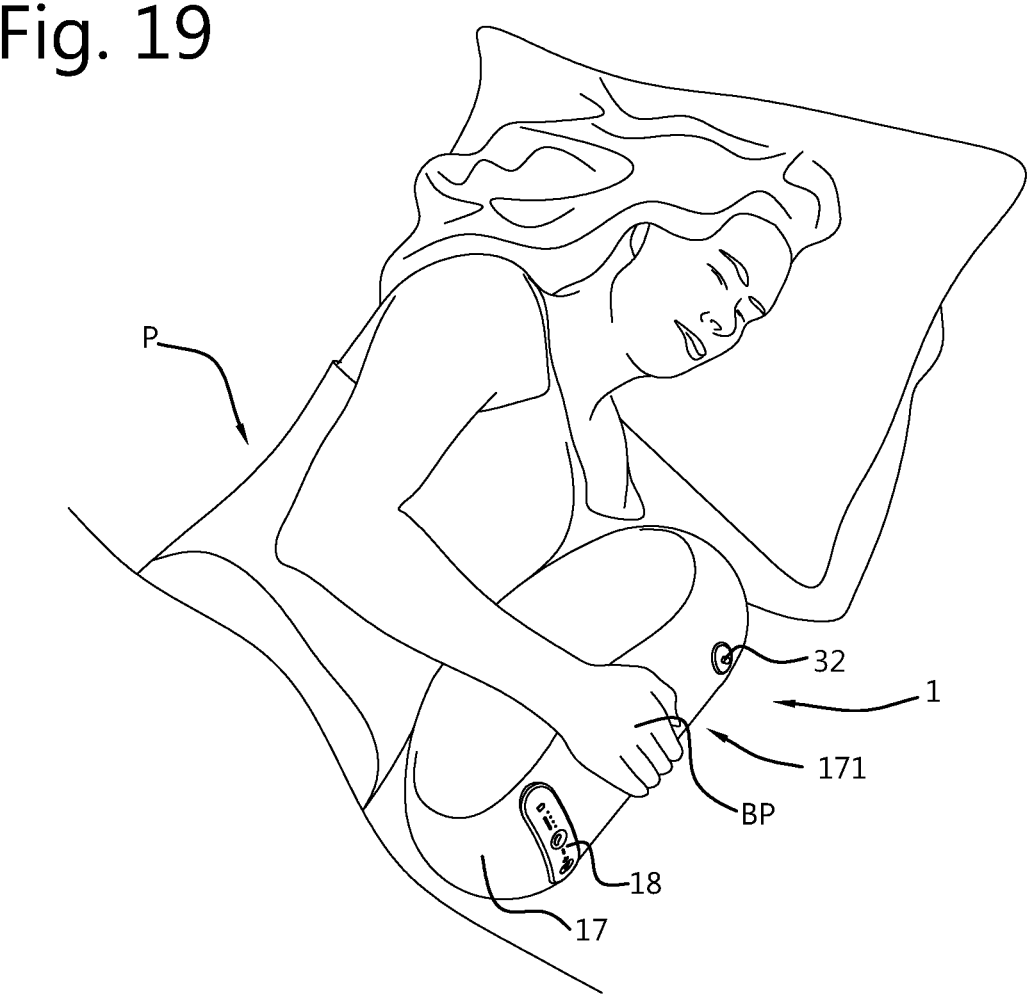
FIG. 19 shows in a schematic view a person in a side posture who is sleeping with a relaxation monitoring device according to the invention.

As in FIG. 1, FIG. 19 shows a person P who is relaxing in a bed. The person is lying on a side and an arm is resting on a relaxation monitoring device 1. In the shown sleeping posture, a hand of the person is positioned at a hand pad 171 of the relaxation monitoring device 1. The hand pad is positioned in such a manner that the person may intuitively attract the relaxation monitoring device 1 close to the person's body. The person P and the relaxation monitoring device 1 are positioned in a so called spooning arrangement. The relaxation monitoring device 1 is configured to be used in this posture when lying in a bed, wherein the relaxation monitor device is oriented in a right manner in front of the user. Once the relaxation monitoring device is correctly oriented in front of the user, the user may shift in position, for example shift an arm along the relaxation monitoring device without affecting the correct orientation.

The relaxation monitoring device 1 has a cushion 17. The cushion 17 includes a pillow-case which is placed around a foam body. Here, the relaxation monitoring device 1 is completely covered by the cushion 17 and forms a hand-pillow. The pillow-case is of a textile material which is comfortable in skin contact and can be removed to be cleaned when desired.

The cushion 17 provides a soft outer surface which forms a cushioning support for a human lower arm and hand BP in a comfortable manner.

Figure 20:
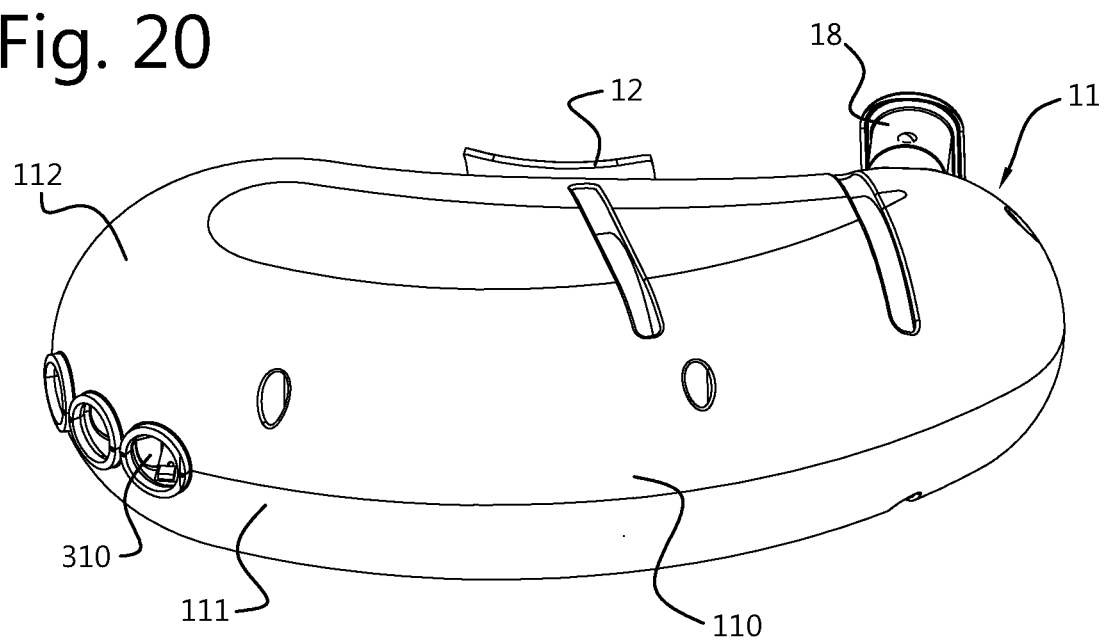
FIG. 20 shows in a perspective view an assembly of the relaxation monitoring device without cushion.

FIG. 20 shows the relaxation monitoring device 1 in further detail without the cushion 17. The relaxation monitoring device 1 has a housing 11 for housing electronic components.

The housing 11 comprises an outer shell 110 which delimits an inner space 119 for containing electrical components, like a battery pack 19, an air-pump 130, a control unit 30 etc. The outer shell 110 forms a hard outer covering. The housing 11 is made of plastic. The housing 11 is manufactured by injection moulding. The outer shell 110 has an upper and a lower half. The outer shell 110 comprises an upper shell section 111 and a lower shell section 112 whose outer contours fit to each other to enclose the inner space 119.

Preferably, all electronic components are housed in the outer shell 110. The housing 11 including the outer shell 111 may enclose at least some of the electronic components which may be beneficial in sound reducing. In addition, the electronic components may be firmly mounted to the housing 11 and shielded by the outer shell 110 which may contribute in preventing damages, e.g. when the relaxation monitoring device is falling from a bed.

Here, the outer shell 110 of the housing 11 determines an outer shape of the relaxation monitoring device. The outer shell 110 is configured to be covered by the foam body of the cushion 17 in which the foam body is formed by a layer. The foam body has a substantially constant thickness. The cushion 17 fully circumvents the outer shell 110.

Figure 21:
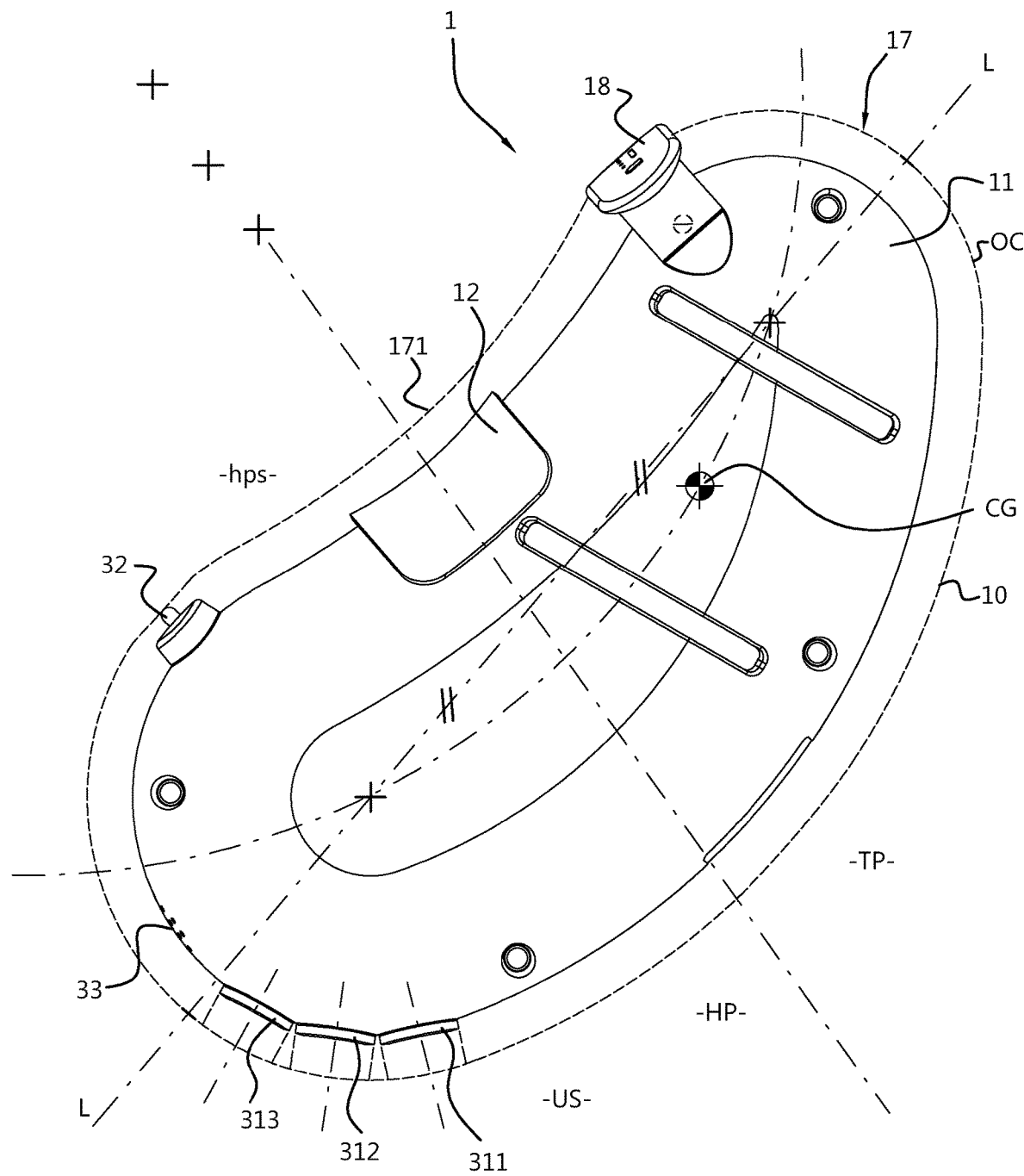
FIG. 21 shows in a top view of the relaxation monitoring device of FIG. 20 an outer contour determining a functional outer shape of the device.

FIG. 21 shows a top view of the housing 11 of the FIG. 20 which top view projection is illustrative for a typical geometrical form of the relaxation monitoring device 1. The housing 11 which is to be covered by the cushion 17 (as indicated by stripes) which cushion 17 determines the geometry of the relaxation monitoring device 1. When the relaxation monitoring device is put away, the device will be in a stable laid away position and the shown geometry can be seen in a projection from above. This top view onto this stable position determines the relevant outer shape 10 of the device 1.

The shown geometry in FIG. 21 has a kidney shape, also called a jellybean shape. Here, the upper shell section 112 has an outer contour which is in parallel with the outer contour OC of the relaxation monitoring device 1. The outer contour of the upper shell section 112 defines the typical outer shape 10 of the relaxation monitoring device.

The housing 11 is elongated along a longitudinal axis L-L. From a functional point of view, the relaxation monitoring device 1 has two halves in the longitudinal direction, i.e. a head portion HP and a tail portion TP. The longitudinal axis L-L extends through an origin of an head portion end face HPe and through an origin of an tail portion end face TPe. The head portion HP has a length along the longitudinal axis L-L which equals a length along the longitudinal axis L-L of the tail portion TP. In a correct use, the relaxation monitoring device 1 has an orientation in which the head portion HP is directed to a face of the user, while the tail portion TP is directed to an abdominal of the user.

Figure 22:
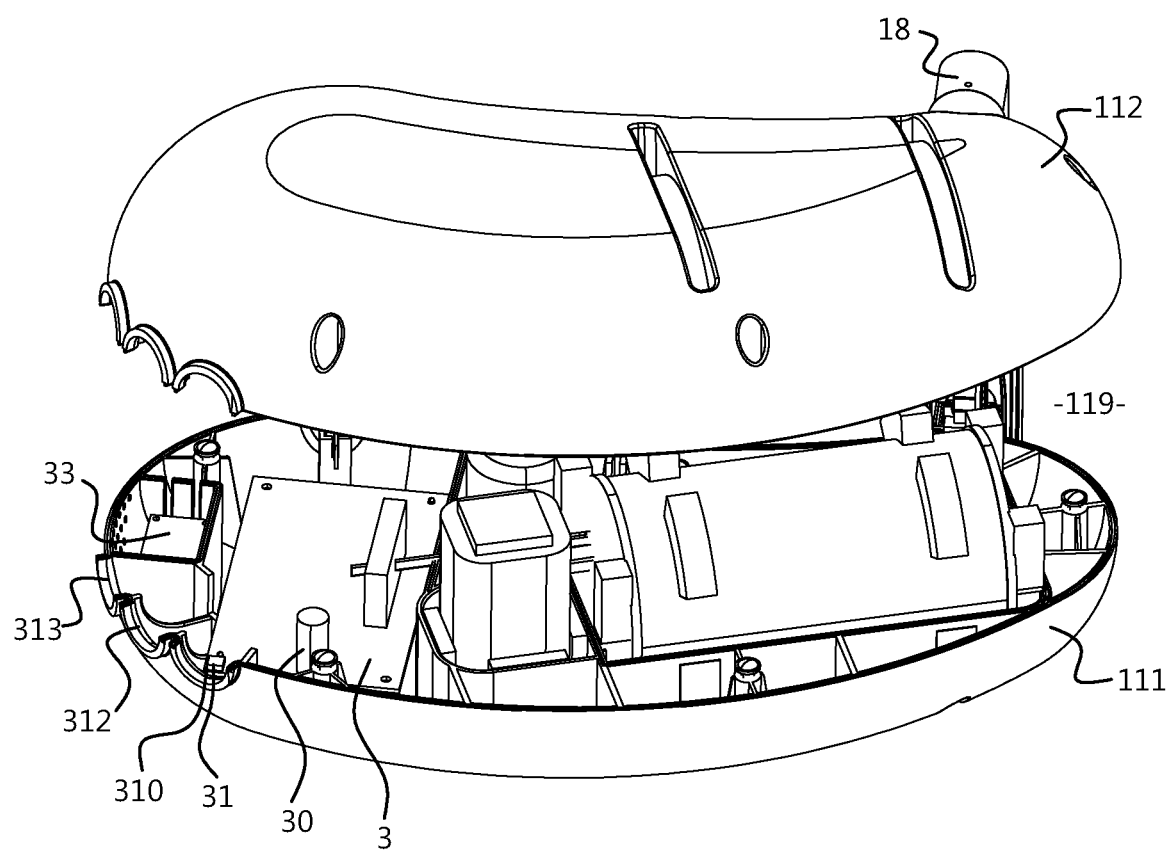
FIG. 22 shows in an exploded view an inner space of the housing containing a plurality of electronic components.
Figure 23:
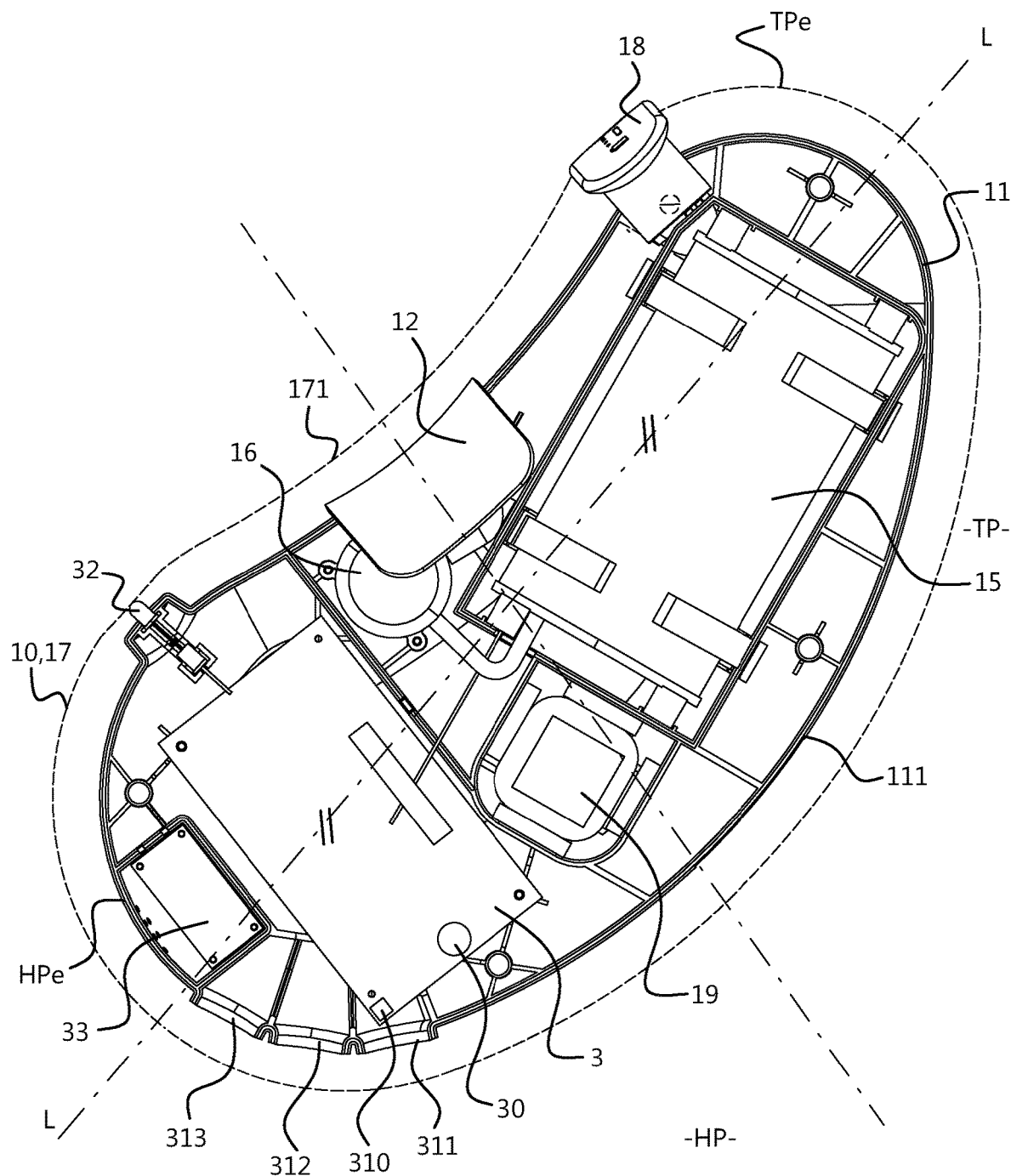
FIG. 23 shows a top view which corresponds with FIG. 21 to illustrate a positioning of the electronic components to obtain a centre of gravity of the device in a tail portion.

As shown in detail in FIGS. 22 and 23, the relaxation monitoring device 1 comprises at least one sensor 31 for monitoring the physiological characteristic of the user. The device may include a temperature sensor and/or an accelerometer as a sensor for measuring vibrations to deduct heart and/or respiration data. Here, the at least one sensor comprises a respiratory sensor 31 for measuring at least one characteristic of a gaseous medium in contact with the sensor. The respiratory sensor 31 is positioned at the head portion HP of the outer shape of the device 1. In particular, the respiratory sensor 31 is positioned in an upper half of the length of the head portion HP along the longitudinal axis L-L. The upper half is positioned adjacent to the head portion end face HPe. The relaxation monitor device 1 further comprises a control unit 30 which is connected to the at least one sensor 31 for receiving a sensor signal from the at least one sensor 31. Both the control unit 30 and the at least one sensor 31 are connected to a printed circuit board 3.

FIG. 20-23 further show at least one air passageway 311, 312, 313 which are provided at the head portion HP. The air passageway 310 is formed by a hole in the housing 11. The hole may have a diameter of at most 5 mm. The at least one air passageway 311 is in fluid communication with the at least one sensor 31. Preferably, multiple air passageways are provided to increase a reach for receiving an exhaled airflow from the user. Preferably, the plurality of air passageways are aligned in an array along the outer contour OC of the outer shell 110.

The at least one air passageway 311 is positioned at a top region of the head portion HP. The at least one air passageway 311 is laterally positioned with respect to the longitudinal axis L-L. The at least one air passageway 311 is positioned at a side of the device which is in a correct use directed to a user. The at least one air passageway 311 is positioned at the so-called user side of the device.

To warrant a proper working of the relaxation monitoring device 1, it is required that the relaxation monitoring device is positioned and oriented by the user in a correct orientation. To obtain accurate measurements by the respiratory sensor 31, the respiratory sensor at the head portion HP should be directed to the face of the user. An upside down orientation and/or inside out orientation should be prevented. The head portion and the user side should be directed to the user's face. The typical geometry of the relaxation monitoring device 1 is provided to obtain the correct positioning and orientation of the relaxation monitoring device by profiting from an intuition of the user.

As shown in FIG. 21, a first feature which contributes to a correct orientation of the relaxation monitoring device 1 during use is formed by a centre of gravity CG which is located in the tail portion TP of the device. The centre of gravity CG is positioned in the tail portion TP of the outer shape. When starting use, the relaxation monitoring device 1 is carried by the user to a place for relaxing. The place to relax may e.g. be a bed, a sofa or a relax chair. When carrying a product, it is a natural tendency to carry such a product in a manner that a centre of gravity is in its lowest position. When lifting up an elongated product, a lightest portion of the product will lift more easy, such that the elongated product will automatically get in an orientation in which the lightest portion is held above. Due to this natural tendency, when it is picked up, the elongated relaxation monitoring device will be held by the user in a predetermined orientation in which the head portion HP is directed upwards, in particular to a face of the user, and the tail portion TP is directed downwards, in particular to an abdominal of the user. The centre of gravity CG in the tail portion TP determines the orientation of the relaxation monitoring device when the user carries the product. Herewith, an incorrect use of the relaxation monitoring device in which the device is oriented upside down may be prevented.

As further shown in FIG. 21, the elongated outer shape 10 of the relaxation monitoring device 1 has an outer contour OC which includes a concave portion which forms a hand pad 171. The hand pad 171 is a second feature of the device which contributes to a correct orientation of the relaxation monitoring device 1 during use.

The hand pad 171 is configured for receiving a hand of the user. The concave portion is dimensioned in correspondence with a human hand. The concave portion has a width which substantially equals a human hand width. The concave portion is positioned at a side of the outer shape which side is in use to be directed away from the user. This side is also called a hand pad side 'hsp'. As shown in the top projection of FIG. 21, the longitudinal axis can be seen as subdividing the outer shape 10 into a user side 'us' for facing the user body and a hand pad side 'hps' for facing away from the user's body. When the user puts a hand onto the hand pad, the user is holding the relaxation monitoring device in an embracing manner. In this posture, the user has a natural tendency to attract the relaxation monitoring device 1 to the user's body. At the same time, by placing a hand onto the hand pad 171, the hand pad side hps is oriented away from the user as it is intended for a correct use. The user side 'us' opposite the hand pad side is directed towards the user's body. Herewith, the presence of the hand pad 171 helps the user to bring the device intuitively in a predetermined orientation in which the user side is directed to the user's body for a correct use of the device.

Due to the positioning of the centre of gravity CG in the tail portion TP and the presence of the hand pad, the at least one air passageway 311, 312, 313 will be correctly directed to a face of the user. An exhaled air flow will be effectively captured by the air passageway and conducted to the respiratory sensor 31. Herewith, the accuracy in measuring the physiological characteristic of the user may be improved.

As shown in FIG. 23, the respiratory sensor 31 may be a $CO_2$ sensor 310 for measuring a $CO_2$ concentration in the exhaled airflow. The $CO_2$ sensor 310 may be a chip-shaped sensor which is mountable on to a printed circuit board (PCB) 3. The $CO_2$ sensor 310 is mounted at a corner of the PCB. The PCB electrically interconnects the $CO_2$ sensor 310 with a control unit 30. The PCB 3 is positioned at the head portion HP of the outer shape 10. The PCB 3 is positioned in the housing 11, such that the $CO_2$ sensor 310 is positioned right behind the first air passageway 311.

As further shown in FIG. 23, the relaxation monitoring device comprises a battery 19. Because of its weight, the battery 19 is preferably positioned in the tail portion TP.

Here, as shown, both the battery 19 and an accumulator 16 are positioned in the head portion HP of the outer shape 10. The relaxation monitoring device further comprises a pump unit suspension 15 for holding a pump unit (not shown). The pump unit suspension 15 has a centre of gravity which is positioned in the tail portion TP of the outer shape 10. The pump unit suspension 15 is a relative heavy component of the device and may form more than 20% of a total weight of the device. The placement of the pump unit suspension 15 in the tail portion may be sufficient to position the centre of gravity of the device 1 in the tail portion TP of the outer shape 10.

The pump unit held by the pump unit suspension 15 comprises a motor for driving a pump which is pneumatically connected to an inflatable air chamber 12. The accumulator 16 is fluidly connected in between the pump unit and the inflatable air chamber 12. The inflatable air chamber forms a stimulator to provide stimuli to a user. The provided stimuli can be used to improve a quality of a relaxation of the user. The inflatable air chamber is positioned close to the outer surface of the device. The inflatable air chamber is positioned under the hand pad 171 to transfer haptic stimuli to the hand of the user.

Shown in FIG. 19 is an embodiment of a sleep induction device for inducing changes during a sleep session of a user P, the sleep induction device comprising a stimulator 12 and two sensors for detecting a physiological characteristic of the user P: a heart rate monitor, and a respiratory sensor 31. The stimulator 12 may comprise a stimulator mechanism (not visible) for frequently expanding and collapsing the stimulator, to provide a stimulating rhythm to the user to influence the user's respiration rate. Many alternative stimulator bodies can however be used, stimulating the user in many different ways, including via light, sound, vibration, temperature changes, or with other stimuli that can be experienced by the user.

The sleep induction device further comprises a housing 11 for housing components e.g. electrical components.

Further, the sleep induction device may comprise a memory, arranged to store values of detected physiological characteristics and provided stimuli during the sleep session and a processing unit.

Further, the sleep induction device may comprise a control unit including a control programme which is programmed to determine a current sleep state of the user, which current sleep state is based on at least one detected physiological characteristic measured by the at least one sensor and which control programme is programmed to generate an initial guidance path to induce a change from the determined current sleep state to another sleep state. The control unit may receive input from the heart rate and respiratory sensor, and may determine the sleep state of the user based upon those inputs.

The sleep induction device is able to influence the sleep state of the user by inducing changes, stimulating the user with successive stimuli and defining a guidance path via said successive stimuli. This guidance path is for example defined by a simulated breathing rhythm of the stimulator.

Any number of guidance paths may be programmed into the sleep induction device, offering various guidance paths to be followed by the user when using the sleep induction device.

In the set-up stage, one of the various guidance paths may be selected as an initial guidance path. The set-up stage may be very minimal and only require answering some questions about, for example, preferred sleep position, estimated time between getting in bed and falling asleep, desired amount of sleep per night, and heart rate in rest. Optionally, some questions may be also be asked to the partner of the user, such as questions related to the frequency of position changes, sleepwalking, and/or talking in the sleep.

Alternatively or additionally, the set-up stage may include wearing the sensors of the sleep induction device during one or several sleep sessions without the stimulator being activated, e.g. for sleep session spanning up to a week or longer, such that the natural guidance path of a person can be measured, and such that an appropriate guidance path can be selected.

When used, the sleep induction device starts with monitoring at least one physiological characteristic of the user. These physiological characteristics may for example include measuring the heart rate, the respiratory rate, the eye movement, noise produced, body temperature, brain wave pattern, or other physiological characteristics.

The values of the detected physiological characteristics of the user during the sleep session are stored in the memory of the sleep induction device.

Based on these monitored physiological characteristics, a sleep state is determined. A single physiological value may be used, or multiple physiological values may be used to determine said sleep state. Often-used sleep stages include full awakeness, non-rapid eye movement sleep (NREM), and rapid eye movement sleep (REM). The NREM sleep can further be categorized in four sleep stages: NREM 1, NREM 2, NREM 3, NREM 4. A multitude of these six sleep stages may be defined as sleep states for each individual user. As such, the term 'sleep state' does not only include the six sleep stages recognized in the sleep literature, but also more refined states in between these stages, personal to a user. A stated before, a change in sleep state is thus not only limited to a change in sleep stage, but may, for example, also include a change in the respiratory rate of the user in REM sleep, changing the state of the user.

By stimulating the user with successive stimuli, an initial guidance path is formed to guide the user from a first sleep state to a second sleep state, such that a change in the sleep state of the user is induced. This change in the sleep state of the user can for example be achieved by gradually lowering the respiratory rate simulated by the stimulator, e.g. in continuous or incremental steps. For example, in guiding the user from full awakeness to NREM 1 sleep, the respiratory rate simulated by the simulation device may be changed slowly, over the course of several minutes or even longer, from 10 breaths per minute to 8 breaths per minute. This stimulates the user to lower the breathing frequency, and induces sleep, lowering the sleep onset latency of the user. During the guiding phase, the physiological characteristics are continuously monitored, to determine if the sleeper is following the guidance path initiated by the stimulator.

The values of the provided initial guidance path and the monitored physiological characteristics are stored in a memory while providing the initial guidance path during the sleep session of the user.

FOR EXAMPLE: When the user steps into bed, e.g. to start a night of sleep, the sensors are activated and start detecting the physiological characteristics of the user. For example, a heart rate monitor and a respiration monitor can be used. The monitors monitor the physiological characteristics of the user and determine that the user is fully awake. To make the user fall asleep, the user is first paced, to relax the user and to synchronise the stimulator with the user. For example, the stimulator may simulate a respiratory rate of 10 breaths per minute, for a continued period of time, e.g. 2-10 minutes. While pacing the user, the heart and respiratory rate of the user are continuously monitored, to determine if the user is synchronizing with the stimulator.

Once it is established that the user and the stimulator are synchronizing, the initially measured heart and respiratory rate, the applied respiratory rate of the stimulator, and the time it took until the user was synchronized are stored in the memory of the sleep induction device. In the next step, the sleeper can be guided from a fully awakened sleep stage to the NREM 1 sleep stage, changing the sleep state of the user.

Figure 24:
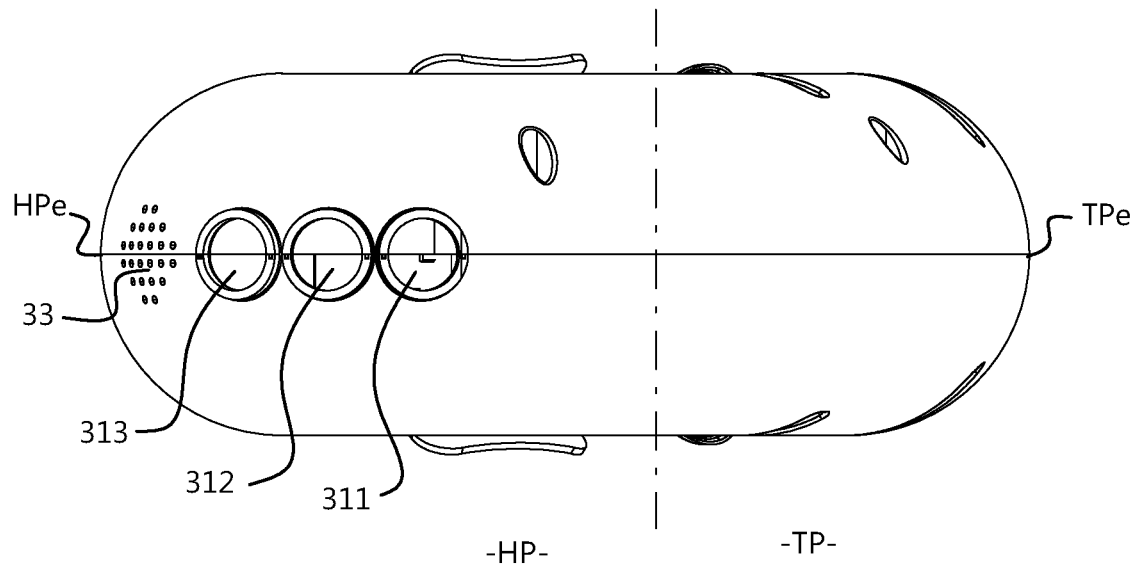
FIG. 24 shows in a side view the user side of the relaxation monitoring device of FIG. 20.
Figure 25:
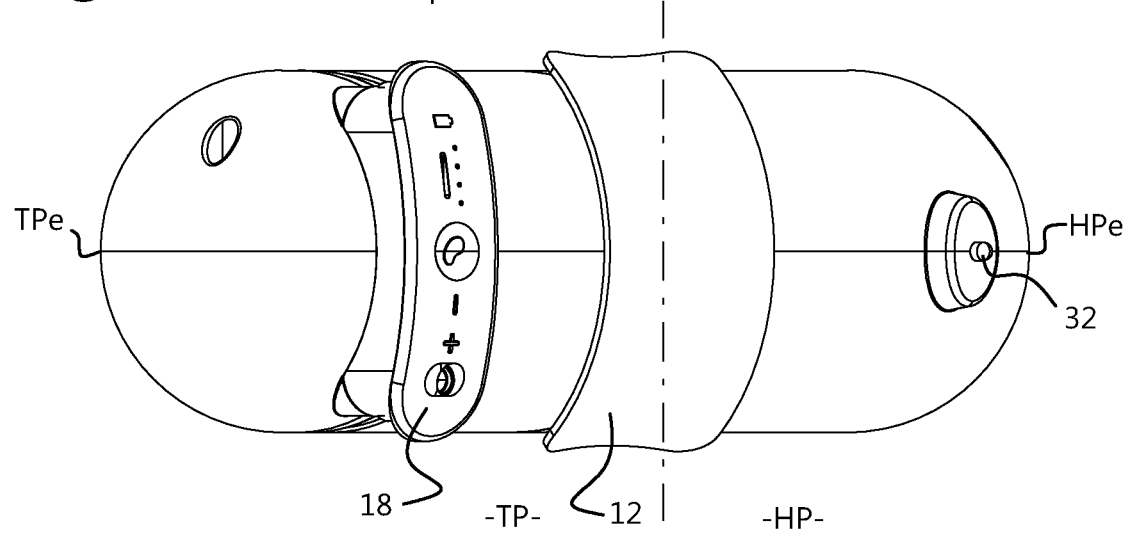
FIG. 25 shows in a side view the hand pad side of the relaxation monitoring device of FIG. 20.

FIG. 24 and FIG. 25 show respectively the user side 'us' and the hand pad side 'hps' of the relaxation monitoring device. FIG. 24 shows the presence of the at least one air passageway 311, 312, 313 at the head portion HP. Further, a speaker 33 for generating sounds is positioned at the head portion HP. The speaker 33 is positioned in between the air passageway and the head portion end face HPe. The speaker 33 can be used to generate an audible stimulus during the relaxing period. The speaker 33 can be used for example to produce successive stimuli to guide a user during a sleep session to manage a sleep pattern of the user. Herewith, the relaxation monitoring device can be used to generate haptic stimuli and in addition audible stimuli to improve a quality in relaxation. Stimuli can be provided to the user based on a measured physical characteristic. The stimuli may assist the user P during a sleep session to improve a sleep quality.

The relaxation monitoring device 1 can be used to assist in falling asleep. A sleep period starts when a user gets into the bed to prepare for a sleep. The relaxation monitoring device is configured to provide successive stimuli to influence a breathing rhythm of the user. The relaxation monitoring device is configured to stimulate a breathing rhythm of the user by providing a haptic stimulus. The haptic stimulus is generated at a position of the hand pad 171. The user senses the stimulus by placing a hand onto the hand pad 171. The haptic stimulus is transferred via the hand to the user.

As shown in FIG. 25, the relaxation monitoring device 1 comprises at least one light emitting element. The at least one light emitting element is positioned at the hand pad side 'hps' of the device for not disturbing the user during a relaxing period. Here, the device 1 comprises an LED 32. The LED 32 is connected to the PCB 3. Further, the device 1 comprises a control panel 18 which also might include a light-emitting element, e.g. a display. The control panel 18 at the hand pad side allows the user to adjust the device before the relaxing period starts.

Thus, in an aspect of the invention, a relaxation monitoring device 1 is provided for monitoring a physiological characteristic of a user during relaxation comprising a cushion 17 which defines an elongated outer shape 10 of the device with a head portion HP and a tail portion TP. The device has at least one respiratory sensor 31 for monitoring an exhaled air flow and an air passageway 311 which are positioned at a user side at the head portion of the outer shape. A centre of gravity CG of the device is positioned in the tail portion TP, such that the device when picked up will intuitively be held by the user in a correct upright orientation. The device includes a hand pad 171, such that the air passageway 311 will be directed towards a face of the user when the user places a hand onto the hand pad 171 and attracts the device towards the user's body.

It is noted that the term "comprising" (and grammatical variations thereof) is used in this specification in the inclusive sense of "having" or "including", and not in the exclusive sense of "consisting only of".

It is further noted that features and aspects described for or in relation with a particular embodiment may be suitably combined with features and aspects of other embodiments, unless explicitly stated otherwise.

Although the invention has been disclosed with reference to particular embodiments, from reading this description those of skilled in the art might appreciate a change or modification that may be possible from a technical point of view but which still do not depart from the scope of the invention as described above and claimed hereafter.

It will be understood by those of skilled in the art that various changes may be made and equivalents may be substituted for elements thereof without departing from the scope of the invention. It is in particular possible to make modifications with respect to the illustrated embodiments which are provided as exemplary embodiments. Modifications may be made within the teaching of the invention and without departing from the scope thereof to adapt a particular situation.

Therefore, the invention is not limited to the particular embodiments disclosed and illustrated in the above detailed description, but the invention will include all embodiments falling within the scope as described above and defined in the appended claims.

Reference list:

| | |
|---|---|
| 1 Relaxation monitoring device | 12 stimulator; inflatable air chamber; air-pocket |
| BP body part; human hand | |
| L-L longitudinal axis | 13 pump unit |
| HP head portion | 130 Pump; diaphragm pump |
| HPe head portion end face | 131 pump outlet |
| TP tail portion | Motor |
| TPe tail portion end face | |
| OC outer contour | 15, 25, 35 pump unit suspension system |
| CG centre of gravity | 151, 251, 351 tubular casing |
| us user side | 1512 tubular casing end |
| hps hand pad side | 1513 tubular casing end |
| P user; person | 1511 circumferential wall |
| | 152, 252, 352 inner suspension |
| 10 outer shape | 1521, 1522, 1523 resilient element |
| 11 housing | 1524 outer circumferential wall |
| 110 outer shell | 1525 inner circumferential wall |
| 111 lower shell section | 153, 253, 353 pair of end caps |
| 112 upper shell section | 1531 protruding walls |
| 119 inner space | 1536, 1537 suction holes |
| | 154, 354 outer suspension |
| | 30 Control unit; processor |
| 14, 16 accumulator | 31 sensor; respiratory sensor |
| 17 cushion; foam body Hand-pillow; | 310 CO2 sensor |
| 171 hand pad | 311 air passageway |
| 18 Control panel | 312 air passageway |
| 181 Display | 313 air passageway |

| Reference list: | |
|---|---|
| 182 on/off button | 32 LED |
| 19 Battery | 33 speaker |
| 3 PCB | |

The invention claimed is:

1. A haptic respiration simulator for relaxing a user by simulating a respiration, the respiration being sensible by a body part of the user, wherein the haptic respiration simulator comprises:
 a housing enclosing components of the haptic respiration simulator;
 an inflatable air chamber, outside of the housing and configured to simulate a respiration by repeated inflation and deflation of the inflatable air chamber;
 a pump unit, in fluid communication with the inflatable air chamber and configured to pump a volume of air into the inflatable air chamber, the pump unit being positioned inside the housing;
 an accumulator configured for accumulating air and for reducing noise originating from a pumping action of the pump unit, the accumulator being in fluid communication with an outlet of the pump unit and with an inlet of the inflatable air chamber; and
 a pump unit suspension system configured for reducing noise originating from operation of the pump unit, the pump unit suspension system comprising:
 a tubular casing configured for receiving the pump unit at an inside thereof, the tubular casing having a substantially closed circumferential wall that prevents at least a part of the sound waves resulting from operation of the pump unit to transfer outside the tubular casing, the tubular casing being positioned inside the housing;
 an inner suspension configured for suspending the pump unit with respect to the tubular casing, the inner suspension being positioned inside the tubular casing, between the pump unit and the tubular casing;
 a pair of end caps configured for sealing the tubular casing, arranged at ends of the tubular casing, and
 an outer suspension configured for suspending the tubular casing with respect to the housing, arranged between the tubular casing and the housing, wherein the noise produced by the haptic respiration simulator is below 40 dBA (decibels A) measured at a position outside of the haptic respiration simulator, at a distance of 25 cm (centimeter).

2. The haptic respiration simulator according to claim 1, wherein the tubular casing is hollow and has open ends, is made of steel and is thick-walled.

3. The haptic respiration simulator according to claim 1, wherein the inner suspension comprises at least three resilient elements, arranged at different positions along the circumference of the pump unit, the at least three resilient elements suspending the pump unit about a central position in an internal volume of the tubular casing formed by the inside thereof.

4. The haptic respiration simulator according to claim 1, wherein the inner suspension comprises a resilient material that surrounds the pump unit, at least in a circumferential direction thereof.

5. The haptic respiration simulator according to claim 4, wherein the inner suspension and the end caps are made of the same material and are integrated with each other.

6. The haptic respiration simulator according to claim 1, wherein the pump unit suspension system comprises a second tubular casing, a second inner suspension and a second pair of end caps for suspending a subassembly of said tubular casing, said inner suspension and said pair of end caps.

7. The haptic respiration simulator according to claim 1, wherein the end caps have a double-walled circumferential wall that protrudes towards the pump unit with the pump unit suspension system in an assembled state, an inner wall of the double-walled circumferential wall being arranged against an inner side of the tubular casing, an outer wall of the double-walled circumferential wall being arranged against an outer side of the tubular casing.

8. The haptic respiration simulator according to claim 7, wherein the outer suspension is formed by said outer wall and/or wherein the inner suspension is formed by said inner wall.

9. The haptic respiration simulator according to claim 1, wherein the outer suspension comprises foam material provided at different locations between the circumferential wall of the tubular casing and the housing.

10. The haptic respiration simulator according to claim 1, wherein the outer suspension comprises a mounting flange connected to the tubular casing or pair of end caps.

11. The haptic respiration simulator according to claim 1, further comprising a second accumulator for accumulating air and for further reducing noise originating from a pumping action of the pump unit, in fluid communication with an outlet of the first accumulator and the inlet of the inflatable air chamber.

12. The haptic respiration simulator according to claim 11, wherein the first accumulator and the second accumulator are both positioned inside the housing, outside of an internal volume of the tubular casing.

13. The haptic respiration simulator according to claim 11, wherein the first accumulator is positioned inside an internal volume of the tubular casing, and wherein the second accumulator is positioned inside the housing, outside of an internal volume of the tubular casing.

14. The haptic respiration simulator according to claim 1, wherein the accumulator is positioned inside the housing, outside of an internal volume of the tubular casing.

15. The haptic respiration simulator according to claim 1, wherein the inflatable air chamber is positioned external of the housing.

\* \* \* \* \*